(12) United States Patent
Yoon et al.

(10) Patent No.: US 11,701,398 B2
(45) Date of Patent: Jul. 18, 2023

(54) **COMPOSITIONS AND METHODS FOR INHIBITING THE PROLIFERATION OF PATHOGENIC *ESCHERICHIA COLI***

(71) Applicant: iNtRON Biotechnology, Inc., Seongnam-si (KR)

(72) Inventors: Seong Jun Yoon, Seoul (KR); Jee Soo Son, Seoul (KR); In Hwang Kim, Gyeonggi-do (KR); Hyoung Rok Paik, Incheon (KR); Hyun Joo Im, Gyeonggi-do (KR); Hyun Jin Yu, Incheon (KR); Beom Seok Kim, Gyeonggi-do (KR); Geun Woo Lee, Gyeonggi-do (KR); Soo Youn Jun, Seoul (KR); Sang Hyeon Kang, Seoul (KR)

(73) Assignee: iNtRON Biotechnology, Inc., Seongnam-si (KR)

( * ) Notice: Subject to any disclaimer, the term of this patent is extended or adjusted under 35 U.S.C. 154(b) by 352 days.

(21) Appl. No.: 16/893,106

(22) Filed: Jun. 4, 2020

(65) Prior Publication Data
US 2021/0379128 A1    Dec. 9, 2021

(51) Int. Cl.
*A61K 35/76* (2015.01)
*A61P 31/04* (2006.01)

(52) U.S. Cl.
CPC .............. *A61K 35/76* (2013.01); *A61P 31/04* (2018.01)

(58) Field of Classification Search
None
See application file for complete search history.

(56) References Cited

U.S. PATENT DOCUMENTS

2014/0356330 A1*   12/2014   Kim .................. A61P 31/04
435/235.1

* cited by examiner

*Primary Examiner* — Oluwatosin A Ogunbiyi
(74) *Attorney, Agent, or Firm* — SIMI Law Group, P.C.

(57) ABSTRACT

A composition for preventing or treating an infection or disease caused by a pathogenic *Escherichia coli* includes a Podoviridae bacteriophage (Esc-COP-30) having an ability to lyse the pathogenic *Escherichia coli* and a pharmaceutically acceptable carrier. A method for preventing or treating an infection or disease caused by a pathogenic *Escherichia coli* includes administering to a subject a Podoviridae bacteriophage and lysing the pathogenic *Escherichia coli* by the Podoviridae bacteriophage.

11 Claims, 4 Drawing Sheets
Specification includes a Sequence Listing.

COMPOSITIONS AND METHODS FOR INHIBITING THE PROLIFERATION OF PATHOGENIC *ESCHERICHIA COLI*

BACKGROUND OF THE INVENTION

Field of the Invention

The present invention relates to compositions and methods for inhibiting the proliferation of pathogenic *Escherichia coli*, more specifically, a composition containing a Podoviridae bacteriophage and a method of using the same.

Discussion of the Related Art

*Escherichia coli* is a Gram-negative, facultative anaerobic, rod-shaped, coliform bacterium of the genus *Escherichia*. It is serologically subdivided according to whether it contains a somatic (O), flagellar (H) or capsular (K) antigen, and these antigens are known to be associated with the pathogenicity of *Escherichia coli*. Pathogenic *Escherichia coli* refers to *Escherichia coli* that has acquired a small number of the virulence factors capable of being expressed in *Escherichia coli*, and, depending on the onset characteristics and the kind of toxin, there are five types of pathogenic *Escherichia coli*, namely enterohemorrhagic *Escherichia coli*, enterotoxigenic *Escherichia coli*, enteroinvasive *Escherichia coli*, enteropathogenic *Escherichia coli*, and enteroaggregative *Escherichia coli*.

Pathogenic *Escherichia coli* causes various diseases, such as food poisoning, acute pancreatitis, urinary tract infection, septicemia and cancer. Among pathogenic *Escherichia coli*-associated cancer, colorectal cancer is one of the most common cancers, accounting for approximately 10% of all cancer cases and approximately 8% of all cancer deaths. Also, colorectal cancer is very common globally and develops through accumulation of colonic epithelial cell mutations that promote transition of normal mucosa to adenocarcinoma. As one of major causes leading to colorectal cancer occurrence, colonic polyp refers to a condition in which the colonic mucosa grows abnormally and becomes a wart-shaped bump that protrudes into the intestine. It is often divided into neoplastic polyps that are likely to develop into cancer and non-neoplastic polyps that are unlikely to develop into cancers. Among various types of polyp, adenomatous polyps are more likely to develop cancer over time. Although diarrhea caused by pathogenic *Escherichia coli* is a notable disease, colonization of some pathogenic *Escherichia coli* is related to promotion of colorectal cancer development by promotion of the formation of adenomatous polyps.

Generally, vaccines and antibiotics are used for the prevention and treatment of infectious diseases of pathogenic *Escherichia coli*. Here, the effectiveness of antibiotics has been continuously decreasing due to the increase of antibiotic-resistant pathogenic *Escherichia coli*, and the development of effective methods other than currently prescribed antibiotics is required.

Recently, the use of bacteriophages as a countermeasure against bacterial infectious diseases has attracted considerable attention. Bacteriophages are very small microorganisms infecting bacteria, and are usually simply called "phages." Once a bacteriophage infects a bacterial cell, the bacteriophage is proliferated inside the bacterial cell. After proliferation, the progeny of the bacteriophage destroys the bacterial cell wall and escapes from the host bacteria, suggesting that the bacteriophage has the ability to kill bacteria. The manner in which the bacteriophage infects bacteria is characterized by the very high specificity thereof, and thus the number of types of bacteriophages infecting a specific bacterium is limited. That is, a certain bacteriophage can infect only a specific bacterium, suggesting that a certain bacteriophage can kill only a specific bacterium and cannot harm other bacteria. Due to this bacteria specificity of bacteriophages, the bacteriophage confers antibacterial effects only upon target bacteria, but does not affect commensal bacteria in animals including human being. Conventional antibiotics, which have been widely used for bacterial treatment, incidentally influence many kinds of bacteria. This causes problems such as the disturbance of normal microflora. On the other hand, the use of bacteriophages does not disturb normal microflora, because the target bacterium is selectively killed. Hence, the bacteriophage may be utilized safely, which thus greatly lessens the probability of adverse actions in use compared to any other antibiotics.

Owing to the unique ability of bacteriophages to kill bacteria, bacteriophages have attracted attention as a potentially effective countermeasure against bacterial infections since their discovery, and there has been a lot of research related thereto.

Bacteriophages tend to be highly specific for bacteria. Because of this specificity, bacteriophages frequently exhibit an antibacterial effect only for certain strains of bacteria, even though the bacteria belong to the same species. In addition, the antibacterial strength of bacteriophages may depend on the type of target bacterial strain. Therefore, it is necessary to collect many kinds of bacteriophages that are useful in order to get effective control of specific bacteria. Hence, in order to develop the effective bacteriophage utilization method in response to pathogenic *Escherichia coli*, many kinds of bacteriophages that exhibit antibacterial action against pathogenic *Escherichia coli* must be acquired. Furthermore, the resulting bacteriophages need to be screened as to whether or not they are superior to others from the aspect of antibacterial strength and spectrum.

SUMMARY OF THE INVENTION

Accordingly, the present invention has been made keeping in mind the problems encountered in the related art and is intended to solve such problems.

In one embodiment, a composition for preventing or treating an infection or disease caused by a pathogenic *Escherichia coli* includes: a Podoviridae bacteriophage having an ability to lyse the pathogenic *Escherichia coli*, and a pharmaceutically acceptable carrier.

In another embodiment, the Podoviridae bacteriophage includes a sequence as set forth in SEQ ID NO: 1 or a sequence having at least 80% query cover with at least 90% identity to SEQ ID NO: 1.

In another embodiment, the Podoviridae bacteriophage has a concentration of $1\times10^1$ pfu/ml to $1\times10^{30}$ pfu/ml or $1\times10^1$ pfu/g to $1\times10^{30}$ pfu/g.

In another embodiment, the Podoviridae bacteriophage has a concentration of $1\times10^4$ pfu/ml to $1\times10^{15}$ pfu/ml or $1\times10^4$ pfu/g to $1\times10^{15}$ pfu/g.

In another embodiment, the pharmaceutically acceptable carrier is lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, or mineral oil.

In another embodiment, the composition further includes one or more selected from the group consisting of a lubricant, a wetting agent, a sweetener, a flavor, an emulsifier, a suspending agent, and a preservative.

In another embodiment, the pathogenic *Escherichia coli* is enterohemorrhagic *Escherichia coli*, enterotoxigenic *Escherichia coli*, enteroinvasive *Escherichia coli*, enteropathogenic *Escherichia coli*, enteroaggregative *Escherichia coli*, or carcinogenic *Escherichia coli*.

In another embodiment, the infection or disease is food poisoning, gastroenteritis, diarrhea, urinary tract infections, neonatal meningitis, hemolytic-uremic syndrome, peritonitis, mastitis, septicemia, Gram-negative pneumonia, shigellosis, dysentery, or cancer.

In another embodiment, the composition is a solution, suspension, emulsion in oil, water-soluble medium, extract, powder, granule, tablet, or capsule.

In another embodiment, the composition further includes a second bacteriophage having an ability to lyse a pathogenic *Escherichia coli* or a non-*Escherichia coli* bacterial species.

In another embodiment, the Podoviridae bacteriophage has major structural proteins in the sizes of approximately 43 kDa, 48 kDa, 63 kDa, 75 kDa, 85 kDa, and 142 kDa.

In another embodiment, the Podoviridae bacteriophage has a latent period of 10-25 minutes and a burst size of 740-860 PFU/infected cell.

In another embodiment, the latent period is 15-20 minutes and the burst size of 770-830 PFU/infected cell.

In one embodiment, a method for preventing or treating an infection or disease caused by a pathogenic *Escherichia coli* includes administering to a subject a Podoviridae bacteriophage; and lysing the pathogenic *Escherichia coli* by the Podoviridae bacteriophage.

In another embodiment, the Podoviridae bacteriophage includes a sequence as set forth in SEQ ID NO: 1.

In another embodiment, the Podoviridae bacteriophage has a concentration of $1 \times 10^1$ pfu/ml to $1 \times 10^{30}$ pfu/ml or $1 \times 10^1$ pfu/g to $1 \times 10^{30}$ pfu/g.

In another embodiment, the Podoviridae bacteriophage has a concentration of $1 \times 10^4$ pfu/ml to $1 \times 10^{15}$ pfu/ml or $1 \times 10^4$ pfu/g to $1 \times 10^{15}$ pfu/g.

It is to be understood that both the foregoing general description and the following detailed description are exemplary and explanatory and are intended to provide further explanation of the invention as claimed.

Advantageous Effects of Invention

The compositions and methods for inhibiting the proliferation of pathogenic *Escherichia coli*, of the present application have high specificity against pathogenic *Escherichia coli*, compared with conventional compositions and methods based on antibiotics. The compositions can be used for preventing or treating pathogenic *Escherichia coli* infections without affecting other useful commensal bacteria and have fewer side effects. In general, when antibiotics are used, commensal bacteria are also damaged, thus entailing various side effects owing to the use thereof. Meanwhile, each antibacterial property of the bacteriophages such as antibacterial strength and spectrum (host range) are different in the case of bacteriophages exhibiting antibacterial activity against the same bacterial species and bacteriophages are usually effective only on some bacterial strains within the same bacterial species. Thus, the compositions and methods of the present application provide different effects in its industrial applications.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
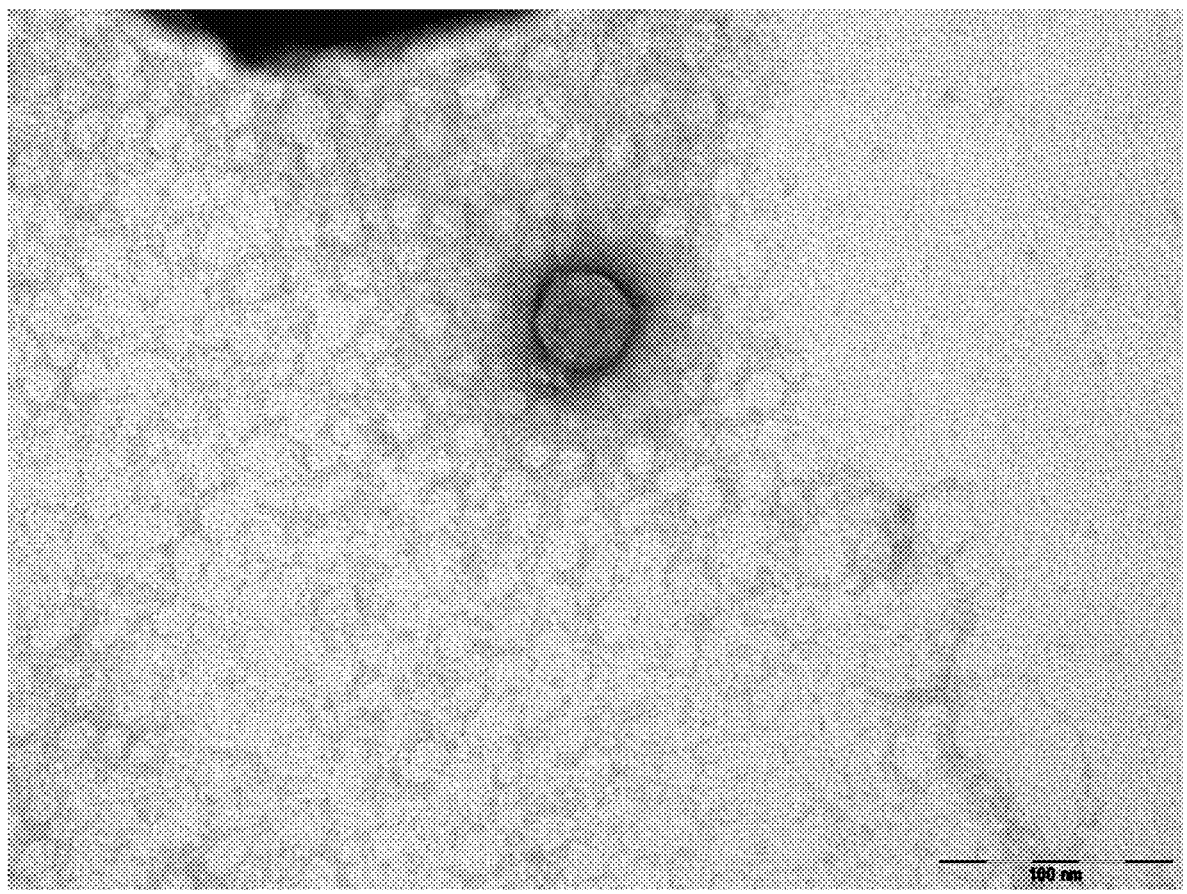
FIG. 1 is an electron micrograph showing the morphology of the bacteriophage Esc-COP-30.

Reference will now be made in detail to embodiments of the present invention, example of which is illustrated in the accompanying drawings.

In accordance with one aspect of the present invention, the present invention provides a Podoviridae bacteriophage, named as Esc-COP-30, which has the ability to specifically kill *Escherichia coli* and has a genome including a sequence as set forth in SEQ ID NO: 1. In some embodiment, the Podoviridae bacteriophage includes a sequence having at least 80% query cover with at least 90% identity, at least 85% query cover with at least 90% identity, at least 90% query cover with at least 90% identity, at least 95% query cover with at least 90% identity, at least 96% query cover with at least 90% identity, at least 97% query cover with at least 90% identity, at least 98% query cover with at least 90% identity, at least 99% query cover with at least 90% identity, or at least 99.5% query cover with at least 90% identity to SEQ ID NO: 1.

The present invention also provides a method for preventing and treating infections or diseases caused by pathogenic *Escherichia coli* using a composition including the same as an active ingredient.

The bacteriophage Esc-COP-30 was isolated by the present inventors and then deposited at Korea Collection for Type Cultures, Korea Research Institute of Bioscience and Biotechnology on Nov. 15, 2019 (Accession number: KCTC 14032BP).

The molecular weight of major structural proteins of the bacteriophage Esc-COP-30 is approximately 43 kDa, 48 kDa, 63 kDa, 75 kDa, 85 kDa, and 142 kDa.

The latent period and burst size of the bacteriophage Esc-COP-30 are 10-25 minutes and 740-860 PFU/infected cell, respectively, preferably 15-20 minutes and 770-830 PFU/infected cell, respectively, but are not limited thereto.

Also, the present invention provides a composition applicable for the prevention or treatment of infections or diseases caused by pathogenic *Escherichia coli*, which include the bacteriophage Esc-COP-30 as an active ingredient.

Because the bacteriophage Esc-COP-30 included in the composition of the present invention kills pathogenic *Escherichia coli* effectively, it is considered effective in the prevention of pathogenic *Escherichia coli* infections or treatment of diseases caused by pathogenic *Escherichia coli*. Therefore, the composition of the present invention is capable of being utilized for the prevention and treatment of diseases caused by pathogenic *Escherichia coli*.

The diseases caused by pathogenic *Escherichia coli* in the present invention include food poisoning, gastroenteritis, diarrhea, urinary tract infections, neonatal meningitis, hemolytic-uremic syndrome, peritonitis, mastitis, septicemia, Gram-negative pneumonia, shigellosis, dysentery and cancer, but are not limited thereto.

The pharmaceutically acceptable carrier included in the composition of the present invention is one that is generally used for the preparation of a pharmaceutical formulation, and examples thereof include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but are not limited thereto. The composition of the present invention may additionally include lubricants, wetting agents, sweeteners, flavors, emulsifiers, suspending agents, and preservatives, in addition to the above ingredients.

In the composition of the present invention, the bacteriophage Esc-COP-30 is included as an active ingredient. The bacteriophage Esc-COP-30 is included at a concentration of $1 \times 10^1$ pfu/ml to $1 \times 10^{30}$ pfu/ml or $1 \times 10^1$ pfu/g to $1 \times 10^{30}$ pfu/g, and preferably at a concentration of $1 \times 10^4$ pfu/ml to $1 \times 10^{15}$ pfu/ml or $1 \times 10^4$ pfu/g to $1 \times 10^{15}$ pfu/g.

The composition of the present invention can be formulated according to a method that can be easily performed by those of ordinary skill in the art to which the present invention pertains using a pharmaceutically acceptable carrier and/or excipient in the form of a unit dose or in a multi-dose container. Then, the formulation may be in the form of a solution, suspension, or emulsion in oil or a water-soluble medium, extract, powder, granule, tablet, or capsule. A dispersing agent or stabilizer may be additionally included.

In order to improve the effectiveness of above purpose, bacteriophages that have antibacterial activity against non-*Escherichia coli* bacterial species may be further included in the composition of the present invention. In addition, other kinds of bacteriophages that have antibacterial activity against *Escherichia coli* may be further included in the composition of the present invention. These bacteriophages may be additionally included so as to maximize antibacterial effects, because each antibacterial property of the bacteriophages such as antibacterial strength and spectrum (host range) are different in the case of bacteriophages exhibiting antibacterial activity against the same bacterial species.

In this description, the terms "prevention" and "prevent" indicate (i) to block pathogenic *Escherichia coli* infections; and (ii) to inhibit the progression of diseases caused by pathogenic *Escherichia coli* infections.

In this description, the terms "treatment" and "treat" indicate all actions that (i) suppress diseases caused by pathogenic *Escherichia coli*; and (ii) alleviate the pathological condition of the diseases caused by pathogenic *Escherichia coli*.

In this description, the term "pathogenic *Escherichia coli*" indicates enterohemorrhagic *Escherichia coli*, enterotoxigenic *Escherichia coli*, enteroinvasive *Escherichia coli*, enteropathogenic *Escherichia coli*, enteroaggregative *Escherichia coli* and carcinogenic *Escherichia coli*, but are not limited thereto.

In this description, the terms "diseases caused by pathogenic *Escherichia coli*" and "pathogenic *Escherichia coli* infections" indicate food poisoning, gastroenteritis, diarrhea, urinary tract infections, neonatal meningitis, hemolytic-uremic syndrome, peritonitis, mastitis, septicemia, Gram-negative pneumonia, shigellosis, dysentery and cancer, but are not limited thereto.

In this description, the term "Latent period" indicates the time taken by a bacteriophage particle to reproduce inside an infected host cell.

In this description, the term "Burst size" indicates the number of bacteriophages produced per infected bacterium.

In this description, the terms "isolate", "isolating", and "isolated" indicate actions which isolate bacteriophages from nature by applying diverse experimental techniques and which secure characteristics that can distinguish the target bacteriophage from others, and further include the action of proliferating the target bacteriophage using bioengineering techniques so that the target bacteriophage is industrially applicable.

In this description, the terms "query cover" and "identity" are related to BLAST (Basic Local Alignment Search Tool) which is an online search tool provided by NCBI (National Center for Biotechnology Information).

In this description, the query cover is a number that describes how much of the query sequence (i.e., the sequence of genome of bacteriophage Esc-COP-30) is covered by the target sequence (i.e., the sequence of genome of the previously reported bacteriophage). If the target sequence in the database spans the whole query sequence, then the query cover is 100%. This indicates how long the sequences are, relative to each other.

In this description, the term "identity" or "sequence identity" was measured for "query cover", and is a number that describes how similar the query sequence (i.e., the sequence of genome of bacteriophage Esc-COP-30) is to the target sequence (i.e., the sequence of genome of the previously reported bacteriophage). More specifically, the terms "identity" or "sequence identity" refers to the percentage of identical nucleotides in the spanned sequence part of the target sequence (i.e., the sequence of genome of the previously reported bacteriophage) or the query sequence (i.e., the sequence of genome of bacteriophage Esc-COP-30) when the query sequence (i.e., the sequence of genome of bacteriophage Esc-COP-30) and the target sequence (i.e., the sequence of genome of the previously reported bacteriophage) are analyzed by BLAST alignment analysis. The higher the percent identity is, the more significant the match.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Isolation of Bacteriophage Capable of Killing *Escherichia coli*

Samples were collected from environmental or clinical samples to isolate the bacteriophage capable of killing *Escherichia coli*. Here, the *Escherichia coli* strains used for the bacteriophage isolation had been previously isolated and identified as *Escherichia coli* by the present inventors.

The procedure for isolating the bacteriophage is described in detail hereinafter. The collected sample was added to a TSB (Tryptic Soy Broth) culture medium (casein digest, 17 g/L; soybean digest, 3 g/L; dextrose, 2.5 g/L; NaCl, 5 g/L; dipotassium phosphate, 2.5 g/L) inoculated with *Escherichia coli* at a ratio of 1/1000, followed by shaking culture at 37° C. for 3 to 4 hours. Upon completion of the culture, centrifugation was performed at 8,000 rpm for 20 minutes and a supernatant was recovered. The recovered supernatant was inoculated with *Escherichia coli* at a ratio of 1/1000, followed by shaking culture at 37° C. for 3 to 4 hours. When the sample contained the bacteriophage, the above procedure was repeated a total of 5 times in order to sufficiently increase the number (titer) of the bacteriophage. After repeating the procedure 5 times, the culture solution was subjected to centrifugation at 8,000 rpm for 20 minutes. After the centrifugation, the recovered supernatant was filtered using a 0.45 μm filter. The obtained filtrate was used in a typical spot assay for examining whether or not a bacteriophage capable of killing *Escherichia coli* was included therein.

The spot assay was performed as follows: TSB culture medium was inoculated with *Escherichia coli* at a ratio of 1/1000, followed by shaking culture at 37° C. overnight. 2 ml ($OD_{600}$ of 1.5) of the culture solution of *Escherichia coli* prepared above was spread on TSA (casein digest, 15 g/L; soybean digest, 5 g/L; NaCl, 5 g/L; agar, 15 g/L) plate. The plate was left on a clean bench for about 30 minutes to dry the spread solution. After drying, 10 μl of the prepared filtrate was spotted onto the plate culture medium on which *Escherichia coli* was spread and then left to dry for about 30 minutes. After drying, the plate culture medium that was subjected to spotting was incubated at 37° C. for one day, and then examined for the formation of clear zones at the positions where the filtrate was dropped. In the case of the filtrate generated a clear zone, it is judged that the bacteriophage capable of killing *Escherichia coli* is included therein. Through the above examination, the filtrate containing the bacteriophage having the ability to kill *Escherichia coli* could be obtained.

The pure bacteriophage was isolated from the filtrate confirmed above to have the bacteriophage capable of killing *Escherichia coli*. A conventional plaque assay was used to isolate the pure bacteriophage. In detail, a plaque formed in the course of the plaque assay was recovered using a sterilized tip, which was then added to the culture solution of *Escherichia coli*, followed by culturing at 37° C. for 4 to 5 hours. After the culturing, centrifugation was performed at 8,000 rpm for 20 minutes to obtain a supernatant. The *Escherichia coli* culture solution was added to the obtained supernatant at a volume ratio of 1/50, followed by culturing at 37° C. for 4 to 5 hours. In order to increase the number of bacteriophages, the above procedure was repeated at least 5 times. Then, centrifugation was performed at 8,000 rpm for 20 minutes in order to obtain the final supernatant. A plaque assay was further performed using the resulting supernatant. In general, the isolation of a pure bacteriophage is not completed through a single iteration of a procedure, so the above procedure was repeated using the resulting plaque formed above. After at least 5 repetitions of the procedure, a solution containing the pure bacteriophage was obtained. The procedure for isolating the pure bacteriophage was generally repeated until the generated plaques became similar to each other in size and morphology. In addition, final isolation of the pure bacteriophage was confirmed using electron microscopy. The above procedure was repeated until the isolation of the pure bacteriophage was confirmed using electron microscopy. The electron microscopy was performed according to a conventional method. Briefly, the solution containing the pure bacteriophage was loaded on a copper grid, followed by negative staining with 2% uranyl acetate and drying. The morphology thereof was then observed using a transmission electron microscope. The electron micrograph of the pure bacteriophage that was isolated is shown in FIG. 1. Based on the morphological characteristics, the novel bacteriophage isolated above was confirmed to belong to the Podoviridae bacteriophage.

The solution containing the pure bacteriophage confirmed above was subjected to the following purification process. The *Escherichia coli* culture solution was added to the solution containing the pure bacteriophage at a volume ratio of 1/50 based on the total volume of the bacteriophage solution, followed by further culturing for 4 to 5 hours. After the culturing, centrifugation was performed at 8,000 rpm for 20 minutes to obtain a supernatant. This procedure was repeated a total of 5 times in order to obtain a solution containing sufficient numbers of the bacteriophage. The supernatant obtained from the final centrifugation was filtered using a 0.45 μm filter, followed by a conventional polyethylene glycol (PEG) precipitation process. Specifically, PEG and NaCl were added to 100 ml of the filtrate until reaching 10% PEG 8000/0.5 M NaCl, and then left at 4° C. for 2 to 3 hours. Thereafter, centrifugation was performed at 8,000 rpm for 30 minutes to obtain the bacteriophage precipitate. The resulting bacteriophage precipitate was suspended in 5 ml of a buffer (10 mM Tris-HCl, 10 mM $MgSO_4$, 0.1% gelatin, pH 8.0). The resulting material was referred to as a bacteriophage suspension or bacteriophage solution.

As a result, the pure bacteriophage purified above was collected, was named the bacteriophage Esc-COP-30, and then deposited at Korea Collection for Type Culture, Korea Research Institute of Bioscience and Biotechnology on Nov. 15, 2019 (Accession number: KCTC 14032BP).

Example 2: Separation and Sequence Analysis of Genome of Bacteriophage Esc-COP-30

The genome of the bacteriophage Esc-COP-30 was separated as follows. The genome was separated from the bacteriophage suspension obtained using the same method as in Example 1. First, in order to remove DNA and RNA of *Escherichia coli* included in the suspension, 200 U of each of DNase I and RNase A was added to 10 ml of the bacteriophage suspension and then left at 37° C. for 30 minutes. After being left for 30 minutes, in order to stop the DNase I and RNase A activity, 500 μl of 0.5 M ethylenediaminetetraacetic acid (EDTA) was added thereto and then left for 10 minutes. In addition, the resulting mixture was further left at 65° C. for 10 minutes, and 100 μl of proteinase K (20 mg/ml) was then added thereto so as to break the outer wall of the bacteriophage, followed by reaction at 37° C. for 20 minutes. After that, 500 μl of 10% sodium dodecyl sulfate (SDS) was added thereto, followed by reaction at 65° C. for 1 hour. After reaction for 1 hour, 10 ml of the solution of phenol:chloroform:isoamyl alcohol, mixed at a component ratio of 25:24:1, was added to the reaction solution, followed by mixing thoroughly. In addition, the resulting mixture was subjected to centrifugation at 13,000 rpm for 15 minutes to separate layers. Among the separated layers, the upper layer was selected, and isopropyl alcohol was added thereto at a volume ratio of 1.5, followed by centrifugation at 13,000 rpm for 10 minutes in order to precipitate the genome. After collecting the precipitate, 70% ethanol was added to the precipitate, followed by centrifugation at 13,000 rpm for 10 minutes to wash the precipitate. The washed precipitate was recovered, vacuum-dried and then dissolved in 100 µl of water. This procedure was repeated to obtain a sufficient amount of the genome of the bacteriophage Esc-COP-30.

Information on the sequence of the genome of the bacteriophage Esc-COP-30 obtained above was secured by performing next-generation sequencing analysis using Illumina Mi-Seq equipment from the National Instrumentation Center for Environmental Management, Seoul National University. The finally analyzed genome of the bacteriophage Esc-COP-30 had a size of 40,403 bp, and the sequence of whole genome was expressed by SEQ ID NO: 1.

The homology (similarity) of the bacteriophage Esc-COP-30 genomic sequence obtained above with previously reported bacteriophage genomic sequences was investigated using BLAST investigation, the genomic sequence of the bacteriophage Esc-COP-30 was found to have a relatively high homology with the sequence of the *Citrobacter* bacteriophage SH3 (Genbank Accession No. KU687349.1) (query cover: 71.5%, sequence identity: 91.5%). However, the topology of the bacteriophage Esc-COP-30 genome is circular, whereas *Citrobacter* bacteriophage SH3 has linear genome. In addition, the number of open reading frames (ORFs) on the bacteriophage Esc-COP-30 genome is 50, whereas *Citrobacter* bacteriophage SH3 has 49 open reading frames.

Based upon this result, it is concluded that the bacteriophage Esc-COP-30 must be a novel bacteriophage different from conventionally reported bacteriophages. Further, since the antibacterial strength and spectrum of bacteriophages typically depend on the type of bacteriophage, it is considered that the bacteriophage Esc-COP-30 can provide antibacterial activity different from that of any other bacteriophages reported previously.

Example 3: Analysis of the Major Structural Proteins of Bacteriophage Esc-COP-30

Figure 2:
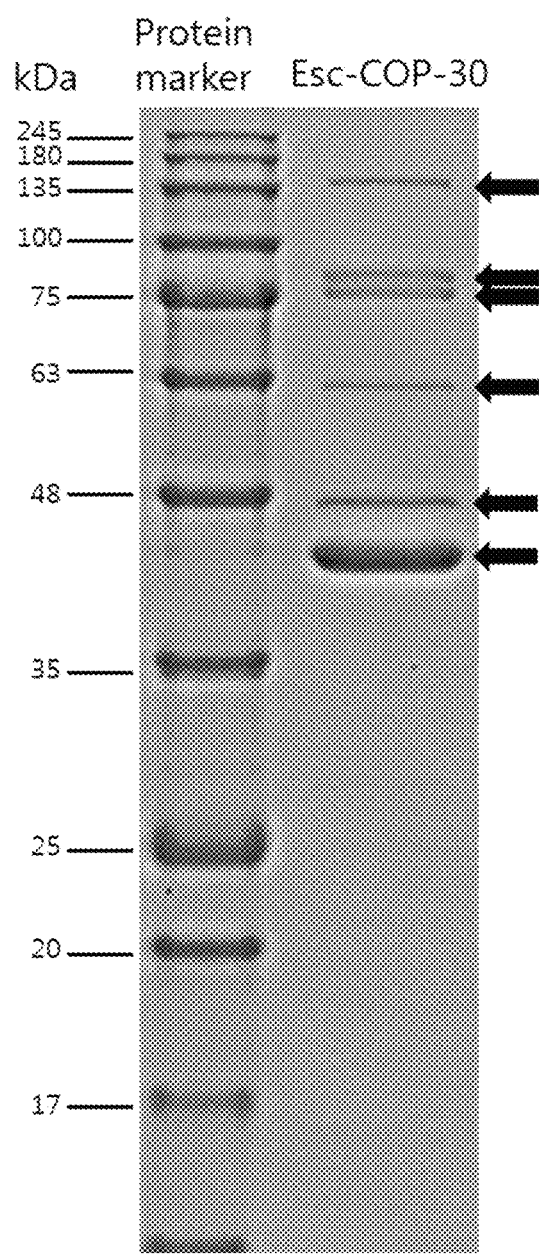
FIG. 2 is a result of the analysis for major structural proteins of bacteriophage Esc-COP-30.

One-dimensional electrophoresis was performed to analyze the major structural proteins of the bacteriophage Esc-COP-30. To obtain the proteins constituting the outer wall of the bacteriophage Esc-COP-30, 200 µl of the bacteriophage suspension prepared in Example 1 was mixed with 800 µl of acetone, which was vortexed vigorously. The mixture stood at −20° C. for 10 minutes. Centrifugation was performed at 13,000 rpm at 4° C. for 20 minutes to eliminate supernatant, followed by air drying. The precipitate was resuspended in 50 µl of electrophoresis sample buffer (5×), which was then boiled for 5 minutes. The prepared sample was analyzed by one-dimensional electrophoresis. As a result, as shown in FIG. 2, the major structural proteins in the sizes of approximately 43 kDa, 48 kDa, 63 kDa, 75 kDa, 85 kDa, and 142 kDa were confirmed.

Example 4: Investigation of Ability of Bacteriophage Esc-COP-30 to Kill Pathogenic *Escherichia coli*

Figure 3:
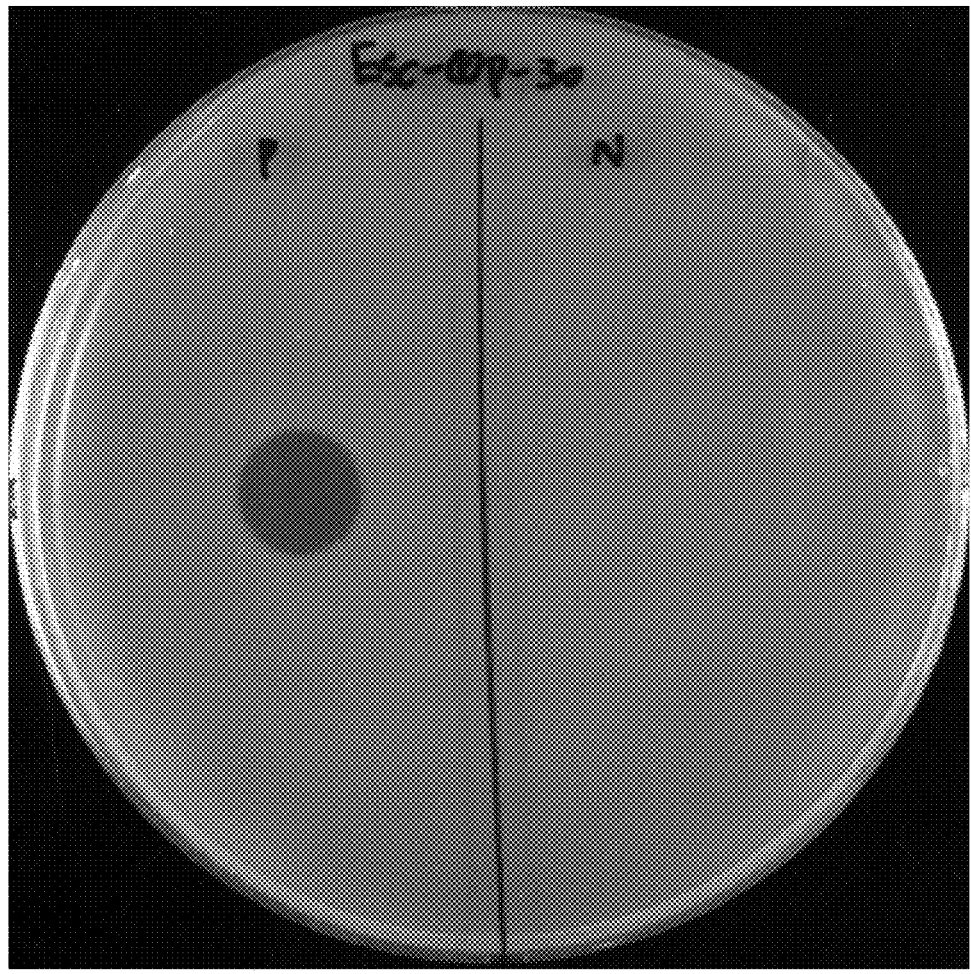
FIG. 3 is a photograph showing the results of an experiment on the ability of the bacteriophage Esc-COP-30 to kill *Escherichia coli*. The clear zone is a plaque formed by lysis of the target bacteria.

The ability of bacteriophage Esc-COP-30 to kill pathogenic *Escherichia coli* was investigated. In order to investigate the killing ability, the formation of clear zones was observed using the spot assay in the same manner as described in Example 1. A total of 5 strains that had been identified as pks positive *Escherichia coli* strains that are positive carriers of the pks genomic island were used as pathogenic *Escherichia coli* for the investigation of killing ability. The bacteriophage Esc-COP-30 had the ability to lyse and kill a total of 3 strains among 5 strains of pathogenic *Escherichia coli* as the experimental target. The experimental result thereof is presented in Table 1 and the representative result is shown in FIG. 3.

TABLE 1

Test of antibacterial activity of bacteriophage Esc-COP-30

| Tested *Escherichia coli* strain | Test result |
|---|---|
| *Escherichia coli* CCARM 1G931 | + |
| *Escherichia coli* CCARM 1G937 | + |
| *Escherichia coli* CCARM 1G938 | − |
| *Escherichia coli* CCARM 1G940 | − |
| *Escherichia coli* CCARM 1G941 | + |

* +: clear lytic activity,
−: no lytic activity;
CCARM: Culture Collection of Antimicrobial Resistant Microbes (Seoul, Korea)

Meanwhile, the ability of the bacteriophage Esc-COP-30 to kill *Bordetella bronchiseptica*, *Enterococcus faecalis*, *Enterococcus faecium*, *Staphylococcus aureus*, *Streptococcus pneumoniae* and *Pseudomonas aeruginosa* was also investigated in a separate experiment. As a result, the bacteriophage Esc-COP-30 did not have the ability to kill these bacteria.

Therefore, it is confirmed that the bacteriophage Esc-COP-30 has strong ability to kill pathogenic *Escherichia coli* and a broad antibacterial spectrum against pathogenic *Escherichia coli*, suggesting that the bacteriophage Esc-COP-30 can be used as an active ingredient of the composition for preventing and treating pathogenic *Escherichia coli* infections.

Example 5: Growth Characteristic of Bacteriophage Esc-COP-30

Figure 4:
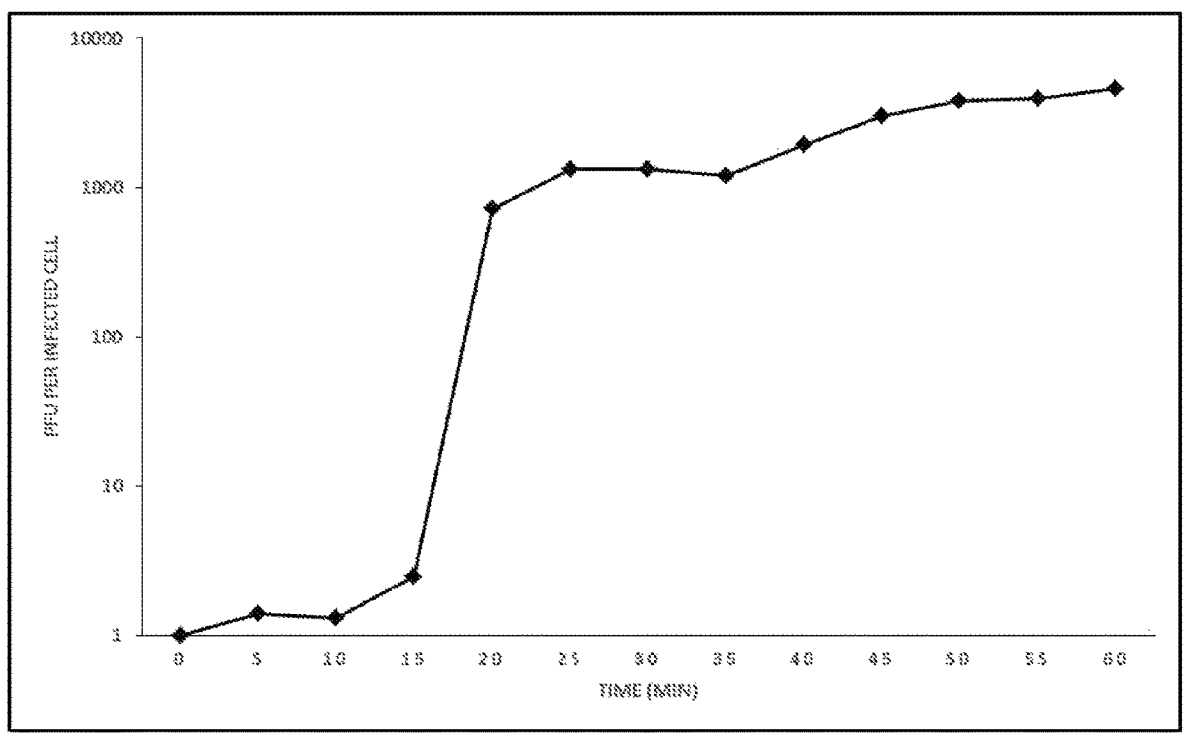
FIG. 4 is the one-step growth curve of bacteriophage Esc-COP-30.

The growth characteristics of bacteriophage Esc-COP-30 was analyzed by one-step growth curve analysis. One-step growth curve analysis of bacteriophage Esc-COP-30 was performed as follows: 50 ml of TSB (Tryptic soy broth, Difco) culture medium was inoculated with *Escherichia coli* at a ratio of 1/1000 and followed by shaking culture until exponential phase ($OD_{600}$=0.3~0.4). Upon completion of the culture, centrifugation was performed at 8,000 rpm for 5 min and a bacterial cell pellet was recovered. The recovered pellet was suspended in 50 ml of TSB. The resulting material may be referred to as a bacterial suspension. The bacteriophage Esc-COP-30 was mixed with the bacterial suspension at a multiplicity of infection (MOI) of 0.1 and incubated at room temperature for 10 min, and then centrifuged at 12,000 rpm for 30 seconds. After supernatants were removed, the pellets containing bacteriophage-infected bacterial cells were suspended in 50 ml of TSB and incubated at 37° C. with shaking. Aliquots were taken at 5 min intervals for 60 min, and the titers in the aliquots were immediately determined by the conventional plaque assay (FIG. 4).

The latent period of bacteriophage Esc-COP-30 was estimated to be approximately 15±5 min with average burst size of about 800±30 pfu/infected cell.

Example 6: Experimental Example Regarding Prevention of Pathogenic *Escherichia coli* Infection Using Bacteriophage Esc-COP-30

100 µl of a bacteriophage Esc-COP-30 suspension (1×$10^8$ pfu/ml) was added to a tube containing 9 ml of a TSB culture medium. To another tube containing 9 ml of a TSB culture medium, only the same amount of TSB culture medium was further added. A pathogenic *Escherichia coli* (pks positive strain CCARM 1G937) culture solution was then added to each tube so that absorbance reached about 0.5 at 600 nm. After pathogenic *Escherichia coli* was added, the tubes were transferred to an incubator at 37° C., followed by shaking culture, during which the growth of pathogenic *Escherichia coli* was observed. As presented in Table 2, it was observed that the growth of pathogenic *Escherichia coli* was inhibited in the tube to which the bacteriophage Esc-COP-30 suspension was added, while the growth of pathogenic *Escherichia coli* was not inhibited in the tube to which the bacteriophage suspension was not added.

TABLE 2

Test for bacterial growth inhibition of bacteriophage Esc-COP-30

| Classification | $OD_{600}$ | | |
|---|---|---|---|
| | 0 minutes after initiation of cultivation | 30 minutes after initiation of cultivation | 60 minutes after initiation of cultivation |
| Bacteriophage suspension was not added | 0.6 | 0.9 | 1.3 |
| Bacteriophage suspension was added | 0.6 | 0.4 | 0.2 |

The above results indicate that the bacteriophage Esc-COP-30 of the present invention not only inhibits the growth of pathogenic *Escherichia coli* but also has the ability to kill pathogenic *Escherichia coli*. Therefore, it is concluded that the bacteriophage Esc-COP-30 can be used as an active ingredient of the composition for preventing a pathogenic *Escherichia coli* infection.

Example 7: Preventive Effect of Bacteriophage Esc-COP-30 on the Infections of *Escherichia coli* in Animal Model Preventive effect of the bacteriophage Esc-COP-30 on weaning pigs affected by *Escherichia coli* was investigated. 4 weaning pigs at 25 days of age were grouped together; total 2 groups of pigs were raised in each pig pen (1.1 m×1.0 m). Heating system was furnished and the surrounding environment was controlled. The temperature and the humidity of the pig pen were controlled consistently and the floor was cleaned every day. From the Pt day of the experiment, pigs of the experimental group (adding the bacteriophage) were fed with feeds adding the bacteriophage Esc-COP-30 at $1\times10^8$ pfu/g according to the conventional feed supply procedure, while pigs of the control group (without adding the bacteriophage) were fed with the same feed without adding the bacteriophage Esc-COP-30 according to the conventional procedure. From the $7^{th}$ day of the experiment, the feeds of both groups were contaminated with $1\times10^8$ cfu/g of pathogenic *Escherichia coli* for 2 days and thereafter provided twice a day respectively for the experimental and the control groups so as to bring about the infections of pathogenic *Escherichia coli*. The administered pathogenic *Escherichia coli* suspension was prepared as follows: Pathogenic *Escherichia coli* (strain CCARM 1G941) was cultured at 37° C. for 18 hours using a TSB culture medium, after which the bacteria were isolated and adjusted to $10^9$ CFU/ml using physiological saline (pH 7.2). From the next day after providing contaminated feeds for 2 days (the $9^{th}$ day of the experiment), pigs of the experimental group (adding the bacteriophage) were fed again with the feeds adding the bacteriophage Esc-COP-30 at $1\times10^8$ pfu/g without contaminating pathogenic *Escherichia coli* according to the conventional feed supply procedure as before, while pigs of the control group (without adding the bacteriophage) were fed with the same feed without adding the bacteriophage according to the conventional procedure. From the $9^{th}$ day of the experiment, diarrhea was examined in all test animals on a daily basis. The extent of diarrhea was determined by measuring according to a diarrhea index. The diarrhea index was measured using a commonly used Fecal Consistency (FC) score (normal: 0, soft stool: 1, loose diarrhea: 2, severe diarrhea: 3). The results are shown in Table 3.

TABLE 3

| | Fecal Consistency score | | | | | |
|---|---|---|---|---|---|---|
| | D9 | D10 | D11 | D12 | D13 | D14 |
| Control group (bacteriophage suspension was not administered) | 2.5 | 2.25 | 1.75 | 1.5 | 1.25 | 1.0 |
| Experimental group (bacteriophage suspension was administered) | 1.25 | 1.0 | 0.75 | 0.5 | 0 | 0 |

From the above results, it is confirmed that the bacteriophage Esc-COP-30 of the present invention could be very effective to suppress the infections of pathogenic *Escherichia coli*.

Example 8: Example of Treatment of Infectious Diseases of Pathogenic *Escherichia coli* Using Bacteriophage Esc-COP-30

The therapeutic effect of the bacteriophage Esc-COP-30 on diseases caused by pathogenic *Escherichia coli* was evaluated as follows: 40 of 8-week-old mice were divided into a total of 2 groups of 20 mice per group, after which subgroups of 5 mice each were separately reared in individual experimental mouse cages, and the experiment was performed for 7 days. On the second day of the experiment, 0.1 ml of a pathogenic *Escherichia coli* suspension was administered to all mice through intraperitoneal injection. The administered pathogenic *Escherichia coli* suspension was prepared as follows: Pathogenic *Escherichia coli* (strain CCARM 1G941) was cultured at 37° C. for 18 hours using a TSB culture medium, after which the bacteria were isolated and adjusted to $10^9$ CFU/ml using physiological saline (pH 7.2). At 2 hr after administration of pathogenic *Escherichia coli*, $10^9$ pfu of bacteriophage Esc-COP-30 was administered through intraperitoneal injection to mice in the experimental group (administered with the bacteriophage suspension). 0.1 ml of saline was administered through intraperitoneal injection to mice in the control group (not administered with the bacteriophage suspension). Both the control and experimental groups were equally fed with feed and drinking water. Whether or not the mice survived was observed daily starting from the administration of pathogenic *Escherichia coli* until the end of the test. The results are shown in Table 4 below.

TABLE 4

| | Survival rate (%) | | | | | |
|---|---|---|---|---|---|---|
| | D2 | D3 | D4 | D5 | D6 | D7 |
| Control group (not administered with bacteriophage suspension) | 100 | 80 | 60 | 35 | 20 | 15 |
| Experimental group (administered with bacteriophage suspension through intraperitoneal injection) | 100 | 90 | 85 | 85 | 80 | 80 |

As is apparent from the above results, it can be concluded that the bacteriophage Esc-COP-30 of the present invention is very effective in the treatment of diseases caused by pathogenic *Escherichia coli*.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

Accession Number

Name of Depositary Authority: Korea Collection for Type Cultures, Korea Research Institute of Bioscience and Biotechnology (Address, 181, Ipsin-gil Jeongeup-si. Jeollabuk-do, 56212; Telephone, (82-63) 570 5604 (82-63) 570 5681; E-mail, patent@kribb.re.kr; Web site, http://kctc.kribb)

Accession number: KCTC 14032BP

Accession date: 20191115

---

What is claimed is:

1. A composition for treating an infection or disease caused by a pathogenic *Escherichia coli* comprising:
   a Podoviridae bacteriophage Esc-COP-30 (deposited in the Korean Collection for Type Cultures (KCTC) under accession number Accession number: KCTC 14032BP) having an ability to lyse the pathogenic *Escherichia coli* and a genome represented by a sequence as set forth in SEQ ID NO: 1, and
   a pharmaceutically acceptable carrier,
   wherein the Podoviridae bacteriophage Esc-COP-30 has a concentration of $1\times10^4$ pfu/ml to $1\times10^{15}$ pfu/ml or $1\times10^4$ pfu/g to $1\times10^{15}$ pfu/g, and
   wherein the composition is adapted for treating the infection or disease caused by the pathogenic *Escherichia coli*.

2. The composition of claim 1, wherein the pharmaceutically acceptable carrier is lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, or mineral oil.

3. The composition of claim 1 further comprising:
   one or more selected from the group consisting of a lubricant, a wetting agent, a sweetener, a flavor, an emulsifier, a suspending agent, and a preservative.

4. The composition of claim 1, wherein the pathogenic *Escherichia coli* is enterohemorrhagic *Escherichia coli*, enterotoxigenic *Escherichia coli*, enteroinvasive *Escherichia coli*, enteropathogenic *Escherichia coli*, enteroaggregative *Escherichia coli*, or carcinogenic *Escherichia coli*.

5. The composition of claim 1, wherein the infection or disease is food poisoning, gastroenteritis, diarrhea, urinary tract infections, neonatal meningitis, hemolytic-uremic syndrome, peritonitis, mastitis, septicemia, Gram-negative pneumonia, shigellosis, dysentery, or cancer.

6. The composition of claim 1, wherein the composition is a solution, suspension, emulsion in oil, water-soluble medium, extract, powder, granule, tablet, or capsule.

7. The composition of claim 1, wherein the Podoviridae bacteriophage Esc-COP-30 has major structural proteins in the sizes of approximately 43 kDa, 48 kDa, 63 kDa, 75 kDa, 85 kDa, and 142 kDa.

8. The composition of claim 1, wherein the Podoviridae bacteriophage Esc-COP-30 has a latent period of 10-25 minutes and a burst size of 740-860 PFU/infected cell.

9. The composition of claim 8, wherein the latent period is 15-20 minutes and the burst size of 770-830 PFU/infected cell.

10. The composition of claim 1 further comprising:
   a second bacteriophage having an ability to lyse a pathogenic *Escherichia coli* or a non-*Escherichia coli* bacterial species.

11. A method for treating an infection or disease caused by a pathogenic *Escherichia coli*, comprising:
- administering to a subject a Podoviridae bacteriophage Esc-COP-30 (deposited in the Korean Collection for Type Cultures (KCTC) under accession number Accession number: KCTC 14032BP) having an ability to lyse the pathogenic *Escherichia coli* and a genome represented by a sequence as set forth in SEQ ID NO: 1; and
- lysing the pathogenic *Escherichia coli* by the Podoviridae bacteriophage,
- wherein the Podoviridae bacteriophage Esc-COP-30 has a concentration of $1\times10^4$ pfu/ml to $1\times10^{15}$ pfu/ml or $1\times10^4$ pfu/g to $1\times10^{15}$ pfu/g.

* * * * *

SEQUENCE LISTING

<160> NUMBER OF SEQ ID NOS: 1

<210> SEQ ID NO 1
<211> LENGTH: 40403
<212> TYPE: DNA
<213> ORGANISM: Unknown
<220> FEATURE:
<223> OTHER INFORMATION: Podoviridae bacteriophage

<400> SEQUENCE: 1

```
tctcacagtt caagaacctc aagtccccccc ataggccctc tttaagtccg accaaaggcc      60
ctacccctag accgaaggtc taaacctcaa gtcactagtc gtcgactagc agccattgac     120
ccgaagtctg acccgaagtc tggaccgata gggcctatat ctagtggttg ggacgatggg     180
ttgggactat atgttgtgtc cctgagtcgc tatctgtatc agcccaaagt catcacctac     240
agtctcacta cctacagtct cactacctac agtctcacta cctagttagc cttcagctaa     300
cctacagtca tcgaccatcg gtaaagccac tacctacagt caccgaccta cagttaatag     360
acacaatcta tagactaag gtctaagaca tgttagtcaa agattatatc ctcttagtca     420
ctatggggcc gacgatagct taatcaatat tatttcaaat tacctattga ctataggtct     480
agactatggc taatagcttc cgtcaacacg acacggcaac aaccggatag tgaagacgcc     540
gggtcagacc ggataagtag tcagcctgta agacatacga acaacaggca tctgacagaa     600
agtagttgac aagcagtaac gaattaaagt agtatgtacc acatcaagtc aacacgattg     660
ataggcagac agaaagtgtt agcttcccgg aattagaagt attagtgacc gggtgttgta     720
acgggtctgc accgctcttt aacaatctgg ataaactctt aatgtgcgcc gatagctagc     780
ttgctagcga tagcgactaa ctacagggtc tttgagtcta catctgaagg ccctgactga     840
tagtcactaa ctataggata aacaagatgg catgatttct aaccaccagt acaacacatg     900
gtctaaccca ttttaaggaa ctacaatcat gaaactgata ggcaaaggcg cgttcactaa     960
gtgctacctg aaggattgcg ggaagcgtgt acttctggtc tcttctgacc cgataaaaga    1020
gtgtatggcg cggggatggt tccctgagtc tccactgttc cctgaagtca agatgattga    1080
ggttggcacg tatgagatgg actacatgcc accaacacga ggtctcaagg cgcatttaga    1140
cgacgaccag tggcaactct atcaggtgct gcgcgattgc tcctcacggt ctccgtatgt    1200
```

```
aatgcgacct gctgacctgt atcccaagtg gtacgagata ttccaagctg cacacgacag    1260
gtccgagtct gagactgtgc gggagggcct gatggatgtt ctgatggcgc tggacgcttg    1320
cgctaacttc gggtcagaca ttcagtttga gataagccca cgtaatgtac gggctgtgga    1380
tggcaagctg atactggttg actgtttctt tcttgtgtcc aagctgcgag aggtgatgtc    1440
atcaagatga taacttatgg tctctgccag caccacgtca ccaacgcccg gcttctggtc    1500
aagaccgggc agttaaacca cgatgcgact atgcgccacc tgaaagcggt ctatgaggga    1560
cgcaagcgca tacacgacag tttgcacgct gaggataagt aaacatgtac cagataactt    1620
atagcagtga acaggcgttc tacgatggat gctacgagat gatgaagcgc ggagcctgct    1680
acgtggctaa tcaccatagc ctgaccataa cgcttacagg cgggtactga tatcttaacg    1740
agtgttaaac tacaggtcat ctacatggtg gcctgactga ttgtcactta accacaagaa    1800
ggaaacacgt aatgaacgca cacgataaag taatcatgaa caacctgatg tctcagcttc    1860
acgctatcat ctgcgaggcg tgctacaaga ctgaagactc aagcgcaggc atagcaggtc    1920
agccgcgctg gggagccttt gagatactgg cccatgagca tggttacaag ctgttaggct    1980
tagggcattt cgctgccgcc tttgagcatg aggacctgcc gggatacgca atcaaggtgg    2040
gctttaagaa agacgactca ggcgctgcgt atgcggcctt ctgccgagag aatgagggca    2100
tggctgggct acctgtcatc catctggtca agcgcttcag cagggcgtac atggtggcta    2160
tggacaagta ccgctcgctg gatgatgttg gtgggaacta ctgccggggc ggtgagactt    2220
atgagcaacg agtcttaaac gtatcgtggc gtgtagtaaa cgcggtgata gactactacg    2280
agaaaccatc tgaggcactt agctggtggc tggaccaaga cgcgcgagct gagtttgcac    2340
acgtcgaggc tcaatatatt aaagaccttg cgcagactgc acgtaagatt cacacgttct    2400
tctacgggct ggcgtcattc gacacgcacc gggctaacgt gatggtcgat aacaacgggc    2460
gcttgataat cactgaccca gtgtcttgga ccgcaagcga ccatcaagac gagatgcaag    2520
gaaagctgaa cgcaatagct gagtgataaa cgagaggcca ctacatctag tggtctcaaa    2580
gattatttct cacaacatat agaggtgaac tatgaacatc tggtactggg tgtgcttatc    2640
tccggtcatc ttcctgatag ctttcggtct tctggatgca atcaagcgag ggtctttcta    2700
atggcttggg cacttctggt catcggctac gggttaatcc tcgcagtcct cacgaaagac    2760
atcgtgaaag cacgtaaagt ctaccgcttc cagtatgtat cactgggccg ctggactgta    2820
agacaaccaa cgggcgcctt ctgcgcaac ctcgcaaacg tctgggacat cgcaacctta    2880
gggagtaaac tgtaatgaac aagtcatacg ggattaatct ggtgcactct atggacgcag    2940
aaatgaacat gttaagccta ctggctaccg ggtatcgtca cggaaagtca agtcacacca    3000
cacgtcaaca gcaggagcgc gaccgtgtac ttcaggcacg actacgggct gagggccata    3060
agtccgaact gatgtgtctg gcgtatggtg gactaccaat cactgacgat ggtaaacttc    3120
tggtctcagg ctggaaggcg ataggccaac ggtcaaccat caagcacacg accaaggtg    3180 acttcagtca tctccacgct aacccactga tatgcaagtg attatgactt aactatcact    3240
ataggactca aggtctaaga ctccaagtga aagaccaaag agactttaaa gtgaaagact    3300
aataacaagg accttaagta tgagcgtcat ctctattgac aaacacgact tctctgacgt    3360
gtcgaacgcc attgagccgt ttaacctgct ggctgaccac tacgggcaag accttgcagt    3420
caaacagctt cagcttgagc atgaggcata cactgaaggc gagcgacgtt tcatcaagaa    3480
ccttgagcgc cagactgagc gcggggaact ggcagacaat caggtcgcca agcctctcat    3540
```

-continued

```
gcagactctg gtccctaaga ttgcgcaagc cgtcaaggag tggcatgaag gtccagacgg    3600
gaagctgtca acctctcgtc ctagcgtagc gttcaccatg ttgagcactg aagagaaggc    3660
cgtcaaggac cgctctctgc gcatctcctg tgagtctgct gcggtcatca tactgaaggt    3720
catcctctcc aagctggtca agcctgaagg gataccgatt acaccgatgg cctccgcgat    3780
aggtcgcaca cttgaggacg aaatccgctt cggtcgcatc cgtgacaagg agaaggagca    3840
cttcaagaag gcgatagctg agaacctgaa caagcgagcc ggggtatcct acaagaaagc    3900
ctacatgcag gcagtcgagg cgtctatgct tgagcagggg caactggctg acgcgtgggg    3960
gacttggagt ccgaccgagg ctgtccacgt aggcatcaag atgctagagc tggtcatcca    4020
gtcatcgcaa ctggtcgagc tgaagcgcta cggtgctggc aatgcagcgg ctgacgtaga    4080
gatggtccac ctgtcagact tctgggtcaa gaagatggca caacgtggct tcagccttgc    4140
aggtatcgcg ccagtctacc aaccttgcgt cgttccacct aagccgtgga ccggggtggt    4200
gggtggtggg tactgggcta aaggtcgcag gcctctaccg ctgattcgct tagggtctaa    4260
ggctgcggtc cagcgctacg aagacgtgta catgcctgaa gtttacgagg cggtgaacat    4320
cattcagcag actccttgga aggtaaacaa gaaggtgctg gaagtggtga acatggtcga    4380
gaagctgaat aacacgccta tcgctgacat ccctcagatg gagccgctga agcctgaaga    4440
ctatgcgggt gagaccgagg aggagcttaa ggcttggaag aaatctgcgg ctggcatcta    4500
tcgacgcgag aaggcccgac agtctcgccg tgtatcgctg agcttcatcg tctcacaggc    4560
taacaagttc tctcagttca aggccatatg gttcccgtac aacatggact ggcgaggtcg    4620
tgtttacgca gtcccgatgt tcaaccctca gggaaacgat atgcagaagg gcctgctgac    4680
tctggcggta ggcaagccaa tcggtgcgga cggcttcaaa tggctgaagg tacacggtgc    4740
aaactgcgcg ggtgtcgata aagtcacctt tgaggacgcg atcaagtggg ttgaggacaa    4800
tcacgacaac atcctagcga ctgctaagag tccgatggat agcattgact ggtggggcca    4860
gttagactct ccgttctgct tcctagcgtt ctgctttgag tatgccgggg tcatgcacca    4920
cgggctaagc tactcatgct ctctgcctat tgcgttcgat gggtcctgct ctgggattca    4980
gcacttcagt gctatgctcc gtgaccacgt tggtggacat gcagtcaacc tgacgccaag    5040
cgggaaggtt caagacatct accgcattgt gtcagaccgg gtggaggaac agcttaagga    5100
gctgctggtc aatggcagtg acaacgaggt gaagaccttt gaggacaaga agacgggtga    5160
gattactgag cgtctggtcc ttgggacccg tgagctggcc cgtcagtggc tgacctacgg    5220
gatgtcacgc tcggtcacta aacgctcggt aatgactctg gcctacgggt cgaaggaata    5280
cgggttcgcg gaccaagtgt ttgaggatac cgtgatgcca gcgattgata gtggcaaggg    5340
cgcaatgttc actgacccaa gccaagcgtc tcgcttcatg gctaagatga tatgggacgc    5400
tgtgagtgtg accgtagttg ctgcggttga cgcgatgaag tggcttcaag gtgctgccaa    5460
gctgctggct gctgaagtga aggacaagaa gactggagaa atcctgaagc cctgccttcc    5520
ggtacactgg gtcacacctg atggtttccc ggtctggcag gaataccgca agaaggatac    5580
cactcgtctg aacctgatgt tcttagggtc attcaacctt cagcctacag tcaacaaagg    5640
cacgaagaag gagctggaca agcacaagca ggagtccggt atcagcccta actttgtaca    5700
ctcacaggac ggcagtcacc tgaggaagac tgtagtccat acccaccgca agtatggcgt    5760
gatgtccttc gcggtgattc acgacagctt tgggaccatc ccagcagacg ctgagttcct    5820
gttcaaggga gtccgcgaga cgatggtcga gacctaccga gacaacgatg ttctgcttga    5880
cttctacgag cagttcgaat accagcttca cgagagccag cgcgacaagt tgcctgagct    5940
```

```
tccgaagaaa ggtaaactga atatcgaaga catcttgtct tcagactttg cattcgctta    6000
ataacacagg agagagacaa catgcaattc gcacaccgtg tatcaaacgt atctggcggc    6060
aacaaggtag tgaccgtaac caaggtggct ggcaagggtc tggtcaaggt tactatggtc    6120
ccgactggaa cggctaaggc caagggtatc agccagaagg agctgattca ggtaatccag    6180
tggtcacacg agaaggccct acgggaagag caaccaaat  gacagaccta cagttactgg    6240
ccctgtggct gggagcactc gcagtattca ctttaatcca acgcagaaga ggttaaccct    6300
aaactatcac tataggatta gactcaaggt catgactcaa agtcgtggcc ttcatgatta    6360
accctaaata acactactg  gagatttaac catatgtatc agaatactat caacttcgag    6420
cgcatccgtg aacgtcagca gactgaaggc tacattccga agggccgcaa gctgaacaag    6480
accaagcgtg gcggtggtgt caagggtgct ttccgtaacg ctgaaggcaa agactcgctg    6540
gttaaccaag agaagtattt cgtaggagcg taagccatga gcagacgttg ttattcgat    6600 gcgtccacga gccagtggtc atcgttaggc cggacccacc gcgagatgag cgaggcagga    6660
cttgaggtcc taatggttga cctgccttac tcccgaatga ctctggtacg aatcattgaa    6720
gcagacggga atcctctggt atcccgcgag tttaccaaac acgaaatctt taactgtgag    6780
caatggtgct tgcagcaact gaatgactat aggagctgga ataatgaca  actatcaaaa    6840 ccaaccctca ccgcgctgta gattactctg agtcaggagt taagaaggcg ctggctgctg    6900
ctgggtctct cgaagctgaa gtgaagtatg atggtgtccg gttgaacctt ccggtgctgc    6960
gagagggtga gacctattgg ctgagccgtg agtctaaacc tcttccagcc ttggagtgga    7020
tgaactctga gttaggcaat gcgtggactc aggccgactg gcggtggttc cttcgtcaag    7080
ctggctatga aggtatcggc ctgatgattg atggcgaggt catggtaaaa ggtgttgact    7140
ttaatacgtc ctcaggtctc attcgaacca agtggctcaa gccaagcaat gagcactacg    7200
ctgagtgcta tccggggcgc ggtaagaagg tcccattctg ggtagcccgg tcacgacttc    7260
aggttgtggt atatggcgtt gtcgatatga caaccatagc agaccagaaa gccgaaggtc    7320
ccatccatag cgtcacacgc ctgaaggccg aagctatcgt ccctctcctc cagaaatact    7380
tcccggaaat cgactgggtt ctgtctgagt cacacacggt ctatgacctt gagtcgctca    7440
actccctgta cgaacagaag cgtctggaag gacacgaggg tctggtagtc aaggacccgc    7500
ttggtaaata caagcgtggc aagaagtctg gcatgtggaa aatgaagcct gaggagacca    7560
tcgacgggac cgtgtgtggc ctcgtgtggg ggactccggg taaggctaac gaaggtaagg    7620
tgattggctt cgaggttctg cttgaggatg gcatggtggt taatgcctgt ggcctgactg    7680
aagaacagaa ggacgagttt acagctaaag tcgctgaatc tagcggttat accttggctg    7740
gcggccctgt ggttattaag gatgggaccg agaagacaaa cccatacgaa ggctggcagt    7800
gtgaagtcct cttcatggag cggttccctg atggctccct tcgtcatccc agcttcaagt    7860
gctggcgtgg aacggaagac aacccaaccg ttaagagtta actaaacgtc aacccagtgg    7920
tcttcggact gctgggtttc tttgcttttgt gctagcaagc tatcgtctgg gccaccagct    7980
agaccctaag ctatcactat aggacaacca tcaacaacct aaggagactc tatgtctaag    8040
aacttaatgt tcaaccgtta ttccagtacc ttccacctgt caaacaaccc gttcgcttgc    8100
attaagcgca acgagaagct gggctacttc gggaaggccg ttaagctgtc acctacagtc    8160
tacgctctga ttactcctgg aaaagttgaa gaggctcgca agaagcgtga gaccaacgta    8220
cctgtggtct acaccaagtg gcctcgcgtt cgtctgttcg ttgagtacat gaaggaggtg    8280
```

```
ttctgattgg atgtatttct tttcttaaag aaagacgaca gttatccata cacacctgta    8340
ataaaggagt taacaatatg aacaaacttg aacaagagat tatcattaag ttggtagata    8400
ataacgaagg tcgcccagat gatttgaatg gctgcggtat tttctgctat aatgttcctt    8460
gcgacctctg ccctgcacat atcaatcaaa agataacctt aggtgaaatc cgagcgatgg    8520
acatacgtaa gcctaaactg gagaaacaag aggtaactcc tacagacgac cagccttacg    8580
ctaaggctat cgacgatggc gtacgcaagc cgtcccacta tcaggtcttt gatggtgtgg    8640
aatccattga gattatcgcc cggtccatga ctgtcagtga gttccgtggt ttctgcatgg    8700
gtaacgtcct gaagtatcga ctcagggctg gtaagaagtc agagctggcg actatggaga    8760
aggacctgaa gaaggctgca ttctatcagg agctgttcga cctgcataaa ggtaagtgct    8820
atgctgccga gtgagtgggc tgagagaaaa tttgaggaga caggtaacgt agattacctt    8880
cagctctaca acttatggaa ggagcgtggt ctatgactga cgtagagaag aaatacatcg    8940
tggagcttga gggtcgcgtt cagtccttcg aggttccggt gtacgcaaag tctcttgaag    9000
aggctaccct gaagtcccaa gagtatgagg acgctgggtt tgttgtcgga cggattcgtc    9060
ctgagaccta aactatcact gtaggacaga cgtccagtta gtaactttaa ataggagatt    9120
tacaccaatg gctaaagagc aactgaagac tttcaccact ccggtagctg gtatcgttga    9180
gccctacgca tggctgaaca aagcagacac caagtttaat gagcgtggtg agcataaggt    9240
taatctgaca ttcgacctga gcaacccgaa ggtccgtaag atgattgatg tcttacagaa    9300
gattcacgac gatgcgtatg cgaaagcact tgcagaccac gagaagaacc cacctcaggt    9360
tcagcgtggc aagaagccta ttgaaccacg agaaggcgac atgccgtgga ttgagaatgg    9420
tgacggtact gttaccatga agtttaaatg ctttgcgtct taccttaaag acggcaagtc    9480
cgagcctatc gtattacggt tctacgacac cgatgctaaa ctcatccgtg acgtcccgaa    9540
tattggcgct gggtctaagc tgaaggtcaa gtttaaagtc ctgccgttca gtggaacgc    9600 tgcgactggt gcaagcgtta agctccagct tgagtcctgc cttctggtag aactgaagga    9660
gtggaaaggt gatggtgctg gtggcgatgg tggctgggt gatgatgaag acctcggtac    9720
tggctacaaa gcgtcaaccg atggtgactt cgggtctgat gacttcggtg acgatggttc    9780
cgaaggaggt gatgaagata cctcaggcga ctacgacttc taaatgacgc tgaaagagaa    9840
actggaggct tactctaagg tttctccttc tggatgctgg gagtggcaac gctcccggac    9900
taaaactggt tatggtcaaa tagctatagg tcatcagaaa caggactatt ctcaccgagt    9960
ttcgtacagg gagcacaaag gtcctatacc tgatggattg ttgttagac ataaatgtga    10020 taacccttgc tgctgtaacc ctgagcacct tgaagttggg actcagaagg acaacatgca    10080
ggactgcgtg aagcggggac gtcactcgaa accgccagta ttcaaaggag aagctaatca    10140
caagactaag ctgaccgagg aagacgtagc gtttatcctg aagtccaagc tgaggcctat    10200
agaacttgct aagatgtttg gcgttactca gcaagctatt aattggagac gcaagaatgg    10260
caagaacgat tagccgaggg catcaagtag gaatatatag gtctggacta gaagcaaaga    10320
accaagagtg gctggagaag aacggagtta aggctgagta cgagatgtat agcatcaagt    10380
acacaatacc agaatccctt cacagttatt gtccagactt tgtactgccc aacgaaatca    10440
ttgtggagac caaaggaatc ttcgcggtgg aagaccgcaa gaagcaccta ttgattagag    10500
aacagcaccc agagttagac attcggttcg tgttctcaag ttcccgctcc aagttataca    10560
aagggtctcc gaccacgtat ggcgcatggt gcgaaaagaa cggctataag tatgccgata    10620
agttcatccc ggttgagtgg ctgagagagg cgactgtacg tctgccttca ggtatactca    10680
```

```
tccctaagaa gaaaggagtt aagtaatgac tcagaaatat aaacttaaag ttagttgctg    10740
cgggtggcct aaaggtacta tcgttacgaa atgtgcgaaa gaccctgaac cattatacgg    10800
acttgttctg gtggaatcca ctgagcgtgg ctactacaaa cacggagcag cagggtatga    10860
cacgcagcct aacggaatgt gggggggcgtg ggtttcagaa ggatatcttg aggaaatctt    10920
agaggataaa cctcaagtcc ctccagcttc gagcgtaccg cctgtgactg tgaagcgtga    10980
agtcctgacc atcaacaaga ttggtgtagg ccagacgttc atcgtccacg gtaagcctga    11040
cgaagtgtac gtgaagatta gcaactccca cgtcttcaac cataagttgc tccagatgca    11100
cagcacggat gctaaccgtt tccaacgtca tctgaaccta gtagctgtag agctggtggt    11160
gtatgatggt gagtgagact cttaggccac gactgcttgc tgggtacgag gtggatgaca    11220
aagggtgctg gaactggaag ggtgcgactg catccggcta cggagtgatt gtccttaaca    11280
ggagggttgc tgctaatcat gaagttggta gaaactacca gactcacagg gcatcctatg    11340
aaatccacca cggcccccatt caagaaggac aggtagtcag gcataagtgc gacaataagc    11400
tgtgcatgaa ccctgagcat ctagaggtcg ggacccagag ggagaacatt caggacgcta    11460
tcgaccgagg tcgtatggcg agtaagctga ctgaggagga cgttgagttc atccggtcat    11520
caacattaag tcaacggagg ttaggtaagc tgctgggcgt aagtccaact gttatctggc    11580
acattcgtaa cggtaacaaa tggaggcacg tttaatggct accaaggtac aattcaagcc    11640
acgtcaatcg acagaggcaa tcttcgtcca ctgttcagcg acccaaccta ctatggacat    11700
cggtcgcgag actattgaaa tgtggcacaa gcagcaggga tggctggcaa tcggatacca    11760
ctttatcatc aaacgtgatg gcactgtgga agagggtcgc ccggtcaatg tcgtagggtc    11820
acacgttaag gactggaact ccaagtccgt aggcgtctgc cttgtagggg gaatcaacgc    11880
caagggtcag tttgaagcta acttcactcc agcccagatg aacgctctac gaaacaagct    11940
ggctgacctg aaggtcctgt atcctcaggc agaaatcaaa gcgcaccatg acgtagcgcc    12000
aaaggcgtgc ccaagtttcg acttacagcg ctggctgtct accaacgaac ttgtaacttc    12060
cgaccacggt taataaactc taaggagaa caactcaatg attaaactta tcgaatttct    12120
tggtcgtctg gtggtgcgtg gttatcgtcg tgctgcggta ctggaacgaa aggtagaaaa    12180
gaagactgct gacggtgcgg ctgatgctgc tgctctggct gacaagctga ccatcgcgtc    12240
actggaagct ggcatgaagg cacgtcaagc tgacaccaaa gctgaccagt tggctaagtt    12300
cttcaaagac taaactatca ccttagggac tggaccgtga atccggtccc tttgtccgca    12360
ttattgatta aggagtgacc aatgtcatac gacgaccaag gcgagagtgt ctttctgtat    12420
cacacccagt gtccagactg tgggtcctcg gatgccaatg tgtttactc agacggccat    12480 caattttgtt atgcgtgtga ccettcagta gcatggaaga aaggagacat ggagttgacc    12540
gagggataca caccctcagg aggtagaaag caagtgagca atctgttaac gttcggtgag    12600
aacgctggac gatatgtccc actaccagcc cgtagtctca gcatggagat atgcaagaag    12660
tacagctact gggtgggtaa catgggtggc aagatggttc aggtcgctga ttattacgac    12720
aggtccggga ccaaggtagg acagaaagtc cgagacgctg agaagaactt cacggctata    12780
ggtagcgtca agtctgacat gctgttcggc tctcagctct ggaacggtgg caagaagata    12840
gtcatcaccg agggcgagat agacgcactg tctgtggctc aggtgcagga cggtaagtat    12900
ccggttgtct ctcttccgtt aggcgctaag tctgcgaaga agctatggc tgcgaacctt    12960 gagtatctcg accagttcga agagataatc ttgatgttcg acatggatga accgggtcgt    13020
```

```
caggccattg aggatgcagc accagtatta ccagcaggtc gggttaaggt tgcgttcatc    13080
aacgggtaca aagacgccaa cgctgcactt caggccaagg acttcaaggc catcaccgat    13140
gctatctgga acgctaaacc tttcgtcccg gctggtgtgg tatcagcatc aagtctgaag    13200
gaccgcacac gagaggtaat gcttaaggca gagactgaag gtctcatgtt ctcgtcatgc    13260
acaacactca acgcgatgac cctaggtgcg cgagctggtg agcttatcat ggtgacttca    13320
gggtcaggca tggtaagtc tacattcgtt cgtcaactcc tcttagagtg gggcagaggt     13380
ggtaaacgtg tgggtatggc tatgcttgaa gaggctgtag aggaaacagt tcaggacctt    13440
atgggtctgg acaataacgt ccgtctacgt cagagcaagg aactgaagca agccatctta    13500
gaggatggtc ggtttgacga atggtacgac aagctgttcg gagacgataa gttccacctg    13560
tacgattcat tcgcagagtc agaggaagac accttgttcg ctaagttagg ctacatggtg    13620
gacggtcttg actgtgacgt catactgcta gaccacatct caatcgttgt gtctggcatg    13680
gaagataact cagatgaacg taagaccatt gaccgaatca tgactcgtct caagaagttt    13740
gcgaagacga agggcgtggt tgtcgttgtc atatgtcacc taaagaaccc agaaaaaggt    13800
aaatcgcatg aagaaggacg acctgtttca atcactgacc tacgtggctc tggtgctctc    13860
cgtcaactgt ctgatactat catcgcccct gagcgaaacc agcaaggtga tactcctaat    13920
attgttcaac ttcgtctgct caagtgtcgt tttacgggtg acactggagt ggcaggacac    13980
ctcgaataca acaagacgac cgggtggctt gaaccgatta gcttcactgg cagcagcgga    14040
gaagaggata gcggctcgtg gaagatacc gacttctaag gaggagtaca ttgctaagaa     14100
aacttaaagc tcgataccat cggttcatgt acaaatggtg gagcgatgaa gcaacctgcc    14160
tgtccaacat tctgggagac caaaggttcg actctaaggc atggaagaaa gctaaccgga    14220
agtttatgta ccacttcttg cgtacagact tctaggtcta gactcaaggt cattcacatc    14280
gagtggcctt tatgattaga cttataacta aaggagaagc aatatgagga cttgcagtag    14340
atgtggctct acaaaggagt ccactgagtt caggaagaca aatgggtggt gcatatcctg    14400
tgttcgtgag gataataggt cgcgatatca tcgaaacaaa ggtacagagg ccggtgaggc    14460
gcatcgccta tctgcccgta agtcttggct taagaaagcc tatggtctca cacttgagga    14520
atatgacact atgttcgata gtcaaaaggg cagatgcgct atatgctcag acattatctt    14580
caagcatggg tctattgaga gtaagaataa tgtagcccac gttgaccatt gccatgactc    14640
aggtattgtt aggggattgc tatgtggtac atgtaatagc gcacttggta agttcggtga    14700
caaggtagcc gtgcttaggg ctgctataaa gtacttggag aaatataatg tttaatctca    14760
actcattcta tggcacagat atagagactg acggtctact agacactgtg tcacagttcc    14820
attgtggtgt tatcattaac gctggaactc aggctactga gaaatatggt gttgcccctca   14880 tgactgggct gacaggtgga ttcaaagagt acatagaccg catagaatct attatggcat    14940
ccactgacgg tatgctggtt ctgcacaatg gtgtgaacta tgatatacca gccttgaaaa    15000
tactgaagaa gaaatacttt ggtaagaacc taaatgtgaa taagggtcga attattgata    15060
ccttggtgct gggccgcttg atgtatccca acattaagtt ctcagacatg ggagcagtga    15120
aagctggtcg tctgccacct aagatgatgg acgccagtc tcttgaggct tggggctatc     15180
gtctcggtga gatgaagggt gagtacaaac acgattacgt tgccaagtgc aaggccgaag    15240
gtatcgaata taaggctggg gacgaatggt tgttcccgtc tcaggagatg ctggactata    15300
acgttcaaga cgttgtggtc acactggcgt tgttcaagaa gttcctgact gacaagtatt    15360
acttccagtc tgaacagttc gctttcgacc agatttatgc gttgcgtctg gaacatgatg    15420
```

```
ctgcgtggac ctgtgcgaag atggaacgta acggctatcc gatgaacacc gagatggtcg      15480
aaggcttata tcgtgaactc accgtcaaac gtgcagagct gctggacaag ctgcgttcga      15540
ctttcggtag ctggtacgca ccaaagggag gcaaggagtt cttcaggcac ccacggacag      15600
gtaaggacct tccgaagtat ccgcgagtcg tgtatcctaa ggttggtggc atctttaaga      15660
agccgaagaa caaagctcaa cgcttaggtc ttgaaccttg tgaacgcgat acgagagaca      15720
cgatggaagg agcaccattc acgccaatca cttacgttga gtttaatccg ggaagcggag      15780
accacttagc gaaagttctg atggagcgtg gctgggagcc tgtggacttc actgacaccg      15840
ggaaacctgt agtcgatgac gagacgttag aacacgttaa gttaccagac gcagaggctc      15900
aggcttgcgt agagctggtc cgtgaatatc tggtggtcca gaagcgcatc ggtcaggctg      15960
ctgaaggtaa gaacgcatgg ttgaaacttg taggtccaga cggacgtatg cacgttcaa       16020 tcaacccatg cggtgcagta accggacgtg cgacccatag ttcaccaaac atggctcagg      16080
tcccggctaa cggtgctcca tatggtgaga cttgccgtgg tgctttcggt gcagcgtgga      16140
acaagactga tggtaagcca gaccttggaa ttcaagtggg tgttgatgcc tcaggtcttg      16200
agcttcgttg tctggggaac cgagcagcac cgtttgatgg tggagcctat gcgaagactg      16260
tggtcgaagg tgacatccac tgggccaacg cagtaaacgc tggattagca cctaacgtcc      16320
cacgcgataa gtcgagccac gaccatgatg ctttccgtaa caacgccaag acgttcatct      16380
atgcgttcct gtatggtgca ggggccgcta agattggact gatagtcggc ggtggtaaga      16440
aggaaggttc agctctcatg aagaaattca ttgagggtac accagccatc aaggacctca      16500
gggaagctgt gagtaatacg ttaatctcag actctaagtg ggtggacggt gagaatatcg      16560
tcaagtggaa acgacgttgg ttgcgtggac ttgatggtcg ccgtatccac atccggtcgc      16620
cacactcagc actgaacgca ctacttcaag gtgatggtgc ggtagtctgt aagcactgga      16680
ttgttgagac tgaacgtatg ctcgaagagg ccgggtatgt ccacggctgg gaaggagact      16740
tcgcttacat ggcatgggtc catgatgaat tgcagattgc agctcgtacc atggagattg      16800
ccgaagatat tcgcaggatt gctcaacttg ctatgcgtaa ggtgggtgag ttctataact      16860
ttaaatgtgt ccttgatacc gaaggtaaga ttggaccaac gtggaaggag tgtcactaat      16920
ggctattact aaacgtattc gtgtaagttt cgacctgaag atggttatta actcaaagga      16980
agaagagacc atgtgtcgcc aactggctga gatgactaaa gcctacgctg agggtgagaa      17040
gctggatggt cttcagttgg ctatggtcaa agcagcaatc gagtcaggac ctgagtctgc      17100
ccttgaaatt gccgtcaaga aggtcatcaa ggaggatctg gtatacgcct ttggtgatta      17160
ccagttcgga gtgtccaacc tgcgattcga ggtcaagcaa tgagtgaata cttacgggtc      17220
ctagcggccc ttaagtcctg cccgaagacc ttccagtcca actatgtgcg caacaacgct      17280
gcacttgtgg ctgaggctgc gagtcgtgga caccttagct gcctgtctat ggatgggcgt      17340
aacaacggtg cgtgggagat taccgctgct ggcaccaagt tcctgaacca acacggaggc      17400
tgcctgtgag cgaaaagaaa atagctctgg tgctggatgg tgactatctg gtcttctctt      17460
ctatggctgc tgccgaggac gagacagact ggggtgatga catctggacc cttatctgtg      17520
accatgagaa ggctcgtcgt atccttgaga acaccatcgc tgaaattgtt aagaagcgca      17580
aggcgtggaa agacgctaag attgtgatgt gctttactga cgataacaac tggcgtaagg      17640
acgttctgcc tacctataag gccaaccgta aaggttctcg caagcctgta ggttacaaga      17700
agttcgtagc agaagtgatg gctgacccac ggttcaacag cttcctgcgt cctacgcttg      17760
```

```
agggtgatga ctgtatgggt atcatcggga cccgacctca gattgttgga tgtgaccatg    17820
cggtgctggt gtcctgtgat aaggacttca agacaatccc gaactgtgag ttcttctggt    17880
taaccactgg tgaaatcctg agtcatacga ctgccgaggc agactactgg cacatggagc    17940
agaccattaa gggtgatact acagatggct atggtggcat tccggggatg ggtgaggata    18000
ccactcgtgc gttccttgac gagccgtact acttcgtaca ggagagccgt gagcttaaga    18060
ccggtaagaa caaaggacag attaagactg agtggaagaa gtatcctaag cgtgaagaca    18120
tgacgctgtg ggactgcatg gtgactctgg ctgctaaagc tgggatgact gaagaagaac    18180
ttctggtcca agctcaggtc gctcgtattt gtcgagcctc cgactacgac cctaagtcca    18240
aggaggtcat actgtggaca ccatccatgt aatctactgg gccggacttc tggcccttta    18300
ctgcatgtat aagtggttcg ggtcgaacaa ccgtcctaaa cactaagtct aaccgatagt    18360
catatcctat caatccaata gtaatccata ggtgaaacac taaactatca ctatagggac    18420
tttaggacct aagatatgac tataagatag attttagtct taacttaaag aggagattca    18480
agatggcgat taatgctatt gaaaacgttg ttaagcagtt acaggaagaa agactcgatg    18540
tcccgaacat ctcacagtct gccatccagt tcctgcacgt actgttcaac gcaagctacg    18600
ctgagaagac gggagctatc agtctcctca agcagcaggg ctacagcgat gcgttcattg    18660
ccgggtttat caagggtctc cagtattgct ctgacactct cgactctgcg attgctatgc    18720
gtcgtgagct gaaagatacc gttcagttcg attaactgta ggagggacta tgtgtttcag    18780
tccaaagatt agcactccga agccttcggt ccaagcacct gaaccagcac ctctgagtga    18840
ggaagttgcg tcagttgaca tcggggctga atcggatgtg acaccaacg agaccaaagg    18900 tatcaaagac ctgaaggtca agaaggagtc tgcacctaaa gataaatcgt cagttagccg    18960
cgctatgcga gcctctggcg tcaacatggg gtaagacaat gctaccatat ctcaactccc    19020
gcgaaggtcg ccacatgtgc gcttgtcgcc tctgggaaga cgggcagtct aacttcaagt    19080
cattcgagga cttcaaggct catacttacc gtatggctga cgagttcgac ggtgaagagt    19140
acacaatcta cgatgtctca ggtcaaccag tagcgtatct ctacatgctg gctaccgcat    19200
cttggcacag accgactccc ggtctggacc ttttcaatagt cgctattcgt cgtgactcgc    19260
agtcctcccg caaggttctt gagactgtca ggcacatcat agacgaagaa tgcaagcgtt    19320
ggggtattag ctggtattct cgtgtcaagc atgtttctgg gtcggtagac atcgtaacaa    19380
ccaagtgcgt tagcatgaac aaggagatta accgtgggta aatcaatcag taaggctttc    19440
aagaaagtag taaaggtgc gttagggacc gttggtcttg gctctgatga cgcgcctaag    19500
gttgttgagg ctcagacccc agcagcacca gtggaagtac cgaacgacaa agtggaggat    19560
gtggatactg aaacaaccgc atctgaggag aagaaagtga agcgttccgg taagcgtagc    19620
cttcaggtct ctcgtacctc tggtggcggt atttctatat gacagactgc atactgcata    19680
agggctgcgt aaataatgct ggatatggtc tgacgtatta acaggtaaaa catggaggca    19740
cgtagatggc taaacgtgaa ggatttgctg ctgaaggcgc gaagtcagtt tatgatagac    19800
tgaagaacgg tagacagccc tatgagacgc gcgctcagaa ctgcgctgct gtcactatcc    19860
cgtcactgtt tcctaaggag tccgacaact cgtctacgga atacgtgacg ccgtggcaag    19920
ctgtaggtgc tcgctgtttg aacaacttgg ctgcaaagct aatgttggca ttattccctc    19980
agtcaccgtg gatgcgactt acagtctccg aatatgaggc caagaccttg agtaatgact    20040
cagaggctgc tgctcgtgtt gacgaagggc tggctatggt cgagcgtgtg ttgatggcct    20100
acatggagac taacagtttc cgtgtcccat tgttcgaagc tctgaagcag cttatcgtct    20160
```

```
caggtaactg tctgctctac attccagagc ctgaacaggg aacctacagt cctatgcgaa    20220
tgtaccgctt agtgtcctac gttgttcaac gtgatgcttt cggtaacatc ttgcagattg    20280
tgactctcga caaggtagcg tttagtgctc taccggaaga cgtgaagtct caactcaacg    20340
cagacgacta tgagcctgat accgagctgg aagtgtatac gcacatttac cgtcaggacg    20400
acgagtatct acgctatgag gaagtggaag gcattgaggt agcagggacc gaaggttctt    20460
acccactgac tgcctgtccg tacatcccgg tacgaatggt tcgactggat ggtgaagact    20520
atggtcgttc ttactgcgag gagtatctgg gagacctgaa ctcgctggag acgattacag    20580
aagctatcac caaaatggct aaggtagcct ccaaggtggt gggcctcgtc aacccgaacg    20640
gtatcacgca acctcgtcgt ctgaataagg cggctacagg tgagttcgtg gctggtcgcg    20700
ttgaggacat caacttcctg caactgacga aaggtcagga ctttacgatt gccaagtcgg    20760
tggctgacgc tatcgagcaa cgtttaggct gggccttcct tcttaatagt gctgttcagc    20820
gtaatgccga gcgagtcact gctgaagaga ttcgttatgt tgctggcgaa ctggaggcga    20880
ccttaggtgg cgtgtactca gtacagtcac aagagcttca gttacctatc gtccgtgtgc    20940
tgatgaacca gcttcagtct gctggcatga ttcctgacct tccgaaagaa gcggtagagc    21000
ctacggtatc cactggtcta gaagcgttag gtcgtggtca ggacttagag aagctaactc    21060
aggcagtcaa catgatgacc ggtcttcagc agctctctca ggacccagac attaacttgc    21120
cgaccctgaa gctgcgactg ctgaatgcct taggcattga tactgctggt ctgcttctga    21180
ctcaggacga gaagatgcaa cgtattgctg aacaatccgc tcaaggagct gtggtcaacg    21240
gtgcgtctgc tgctggtgca acatgggtg ctgctgtagg tcagggagct ggtgaggaca    21300
tggctcaagc ctaaactatc actataggaa caacacaact tgagtgagtg aacgcatggc    21360
cagccgtaac tgactggcag gttgttgtgt ttcctattaa ctaccaaagg agaatgactc    21420
aatgtctcaa tcagtttatg ccgagttcgg cgttagctct aatgcaatca ctggttccgt    21480
tgaggacctg aacgaacacc agaagtctat gcttgaacag gacgtagctg ttcgtgatgg    21540
cgatgacgct attaccttca agcaactgga agctgaaaat gaagaggcga ccgaagaaga    21600
cgaaaacgtc gaagagactg aaggtgaaga agaccacgag tcagatgacg aagcgtctga    21660
gaccgatggt gctcagcctg agttcatcga actgggtgat gcaccaaaag agctgaccga    21720
aagtgtaaca gctctggatg aaaacgaagc tgcattcgat gacatggtgt cttctgctgt    21780
agaagctggc aaggtcactg ctgacgaaat taccgctatc aaggctgaat acgccaagga    21840
cggtaagctg tctgacgcat cctacgctaa gttgcaggaa gcaggttata ccaagcgttt    21900
cgtagattcg tttgtccgtg gtcaggaagc tctggctgaa cagtatgctg ctggtgtggt    21960
tcgctatgct ggtggtgctg aacagtttaa tcgcatcctg tcacaccttg agtccaacga    22020
cccgtcaact cgtgaggcac tggaagctgc tatcgttcgt aaggacattg cgactaccaa    22080
agctctgctg aatctggctg gcaagactct gggtaaagct gtgggtgtta aacctcagcg    22140
taccatcacc actcaggcta aacctgtggt cgcacctaag gctcctcaga ccgaagcatt    22200
cagctctaag gctgacatga ttaaggctat gagtgacccg cgatacctgc gtgacgctaa    22260
gtacacgatg gaagttcgcg ctaaggtagc tgcatcaagc ctgtagttga ctaaactatc    22320
actataggga gaccaagaga ctctgaaagg aagagactca atgtttccct attacttcag    22380
tccatacgga ttgggcgtac agtaagtaat aaactttatc tttcaattga ataggagaat    22440
tatcatatgg caaacgttcc gggtcagaaa attggtacag accaaggtaa aggcaaatcc    22500
```

```
agttccgacg ctctggcgtt gttcctgaag gtatttgctg gtgaagtcct gaccgcattc    22560
actcgccgct ctgtaactgc cgacaagcat attgtccgta ccattcagaa cggtaagtct    22620
gctcagttcc cggtcatggg tcgcacctct ggtgtgtatc tggctccggg tgagcgactg    22680
tccgataagc gtaaaggtat caaacatacc gagaaagtga ttaccattga tggtctgctg    22740
acttccgatg tgatgatttt cgacattgaa gacgccatga accactacga tgtggctggc    22800
gagtattcca accagctcgg cgaatctctg gctattgctg ctgatggtgc ggtactggct    22860
gagatggcga gtctgtgtaa cctcccggct gcatccaacg agaatattgc tggtctgggc    22920
actgcgtccg tacttgaagt aggcaagaaa gctgacctca cacccccggc taaactgggt    22980
gaagcaatca tcggtcaatt gacaattgct cgtgcgaagt tgacctccaa ctacgttcct    23040
gctggcgatc gttacttcta caccacgccg gacaactact ccgcgattct ggcagccctg    23100
atgccgaacg ctgctaacta cgctgcgctg attgaccctg agcgggcaa catccgtaac    23160 gtaatgggct tcgttgtggt tgaggttcct cacctgacgc agggtggtgc tggcgaaact    23220
cgtggtgacg atggtatctc cattgcttcc ggtcagaaac acgccttccc agctacttct    23280
actggtgatg ttaaagttgc tctggacaac gttgtgggcc tgttctctca ccgttctgct    23340
gtgggtactg tgaagctgcg tgacttggcg ctggaacgtg accgtgacgt cgatgctcag    23400
ggcgacctga ttgttggtaa gtacgctatg ggtcacggtg gtctgcgtcc tgaagcggct    23460
ggcgcactgg ttttcagccc agcggcgtaa gcacctttag ccaacctaac gtcgctacag    23520
tagcggctgc acctgaagag gagactctaa ctcctcaaca gaaagctgcg cgtactcgtg    23580
ctgcgaacag ggccgctaaa ctggctgagt ccaacaacta attgaaaccc cttgggtgcc    23640
ttcgggtgct tgaggggttt tttgcttaaa gtgagaggag acttatggct caatacattc    23700
cactgaacgc taacgatgac ttagatgcca tcaacgatat gttagctgct atcggtgaac    23760
cagcagtcct acagcttgac gaagggaacg ctgacgtctc gaatgctcag cgtatcctgc    23820
atcgtgtaaa tcgtcaggtc caagctaaag gctggaactt taacatcaac gaagctgccg    23880
tcctgacacc tgatgtccaa gacaatagga ttagattcct accgtcttat ctccgggtca    23940
tgactgctgg tgctaccagt tactacagca acatgggagg ataccttat gacctgtcca    24000 ctcagtccac gaccttcact ggtccaatta cagttgaact ggtagagatg aaaccgttcg    24060
ctgagatgcc tgtggtcttc cgtgattaca tcgtgaccaa ggcaagccgt gagttcaacg    24120
ctaagttctt cggtagccca gagtctgaac tatatcttcg tgagcaggaa gcagaactct    24180
accagcaggt gatggagtac gagatggaca ctggtcgcta caacatgatg tctgacatag    24240
ggagggacta atggcctacc attacctgaa gattgaccct gagttctttg agcctgttat    24300
ctcaggacta aagactgctg agctgagact caacgacagg gactataagg ttggcgactg    24360
gctaatcctg cgcgagtggc agaacggcta cacagggcag caggtagcac gaaaggtcgt    24420
tcacatagct gaggtagact tcgtgtctcc cggatacgtt ctaatgagca tcatctaaag    24480
gagggcttat gccgctttac acacaaagta tcaagaacct aaagggtggc atgagccaac    24540
agcctgacat cctcaggttc aagaccaag ggtcacttca ggtaaacgct tggtcatctg    24600
aaagcgaggg gctacagaag cgcccaccta cagtctggaa acgtcgagta gctaacgagg    24660
ctgacatccc tgataacgct aagttccacc tgattaaccg tgacgagaac gagcaatact    24720
acgttgtgtt caccggccag acgataaaag tattcggact tgatggaaca gaatacgttg    24780
tcaacggagg gtcaacctac ctatcgtccg caaaccctca ggcagacttc agggtggtga    24840
cggtcgcaga ctatacgttc atcgtcaaca gacgtgtagt tgtttcagca ggtacagcgg    24900
```

```
ttagccaccc cggttatgac atgaagcatc gcgctctgat taacatacgt ggtggacaat    24960
atgggcgcac ccttaccgtc tcaattaatg gtggaccagc tgtatcccat gtccttccga    25020
atggtagtaa tgctgagact gaccctccaa aggtagatgc ccagaacata ggcttcgagc    25080
ttcgagcact tctggtagca gcttatccaa cctacacgtt caacttaggg tctggataca    25140
ttgagattat tcctcctgat ggtaccaaca ttagcagcgt ggagacagcg gatggttatt    25200
ctaaccagtt aatcaacgca gtgttggaca ccgtacagag tgtgagtaag ttaccactag    25260
ccgcacctga cggctacatt atccgaatcc aaggcgagac gaacagttct gctgacgaat    25320
acttcgtaag gtacgatgcc tctcgtaaga cttggcggga gactgtggag ccgggagtgg    25380
taacgggtct ggaaccgggg actatgccac atggtctaat cagaaagtct gacgggagct    25440
ttgactttac gtctctggat tgggcaggac gtggcgcagg caatgatgat actaacccta    25500
tgcctagctt tgtgggtgga actatcaatg acgtgttctt ctaccgaaac agactgggat    25560
tcctgtcttc cgagaacatc atcctgtcac gctcagcaag ctacttctcg ttcttcccta    25620
agagtgtagc gacattaagt gatgacgacc ccattgatgt agccgtgagt cacccacgaa    25680
tctcaatcct gaagtatgcc gtaccgttca atgaacagct ccttctgtgg tctgacgagg    25740
ttcagttcgt gatgacaagc tctggggtac ttacctcaaa gtccatccag cttgacgtag    25800
gatcagagtt cgctgtaagc gatgatgccc gaccttacgc tgttggacgc tctgtcttct    25860
ttagtgctcc tcgtgggacg ttcaccagca tcaaccgata ctttgcgatg gctgatgtaa    25920
cggacgttaa ggacgctgac gatgtgactg ggcacgtatt gtccctcatc cctaacggag    25980
tgttcgatat acaagggtcc tcgactgaga acttcatagc agtgactacc agcggtgcaa    26040
ggtctaaggt ctacatctac aagttcctgt tcaaggaggg cgtgcaactt caggcatctt    26100
ggggcatctg ggactttggc gagtacggag actgtaaggt tctggcaact gcttgtatcg    26160
ggtccaccat gtatctggtt cgtaagtcga ccaagggtat tgactttgag catctgacct    26220
tcatcaagga ctccacggat attcaaggtg agccttatcg tattcacgct gatgccaagg    26280
ttgactacat cattccagcc agtggttacg acatacagaa gaatcagaca acgttcgaca    26340
tcactcaggc atacggtaag attccagcca acggtatcta ccagattgtc gccgctgacg    26400
gtcgctgtgt acgactccca gagcaggact tcatgtttga gcctaacgta gctatcaatg    26460
gtaactgggg aggactgagg gtcttcatag gccgcgtctt caagatgacc tatgagttct    26520
ctaagttcct catcaagcag gaggaccaga acggtacgca gactgtggac acagggcgtc    26580
tacagcttcg cagggcatgg attaactatc aggatacagg cgctatgata ctgaaggtta    26640
agactccagc gcgtgagttt gagaacactc tcaacggcta aagctgggc cagcagacca    26700 tcgggtctgt gagcattggg tccgggcagt ttaggttccc tatgaacggc gacgccaccc    26760
acacgactct gacactagag tccgactatc ctaccccagt gtccatcgta gggtgtggct    26820
gggaggcttc atacgcgcgt aaagcgaagt ctatctaact tactgattgg cctatagatt    26880
caccttaact atcactatag ggactatagg ccctttaagt tataatactt taagaggaga    26940
ctttatgtat attcgtaaag ctacggaacc ggatgtccac tactttatgt ggcatctttc    27000
agcagatgac gttaaggagt gcaaagcaaa ctacgggtca accgtgggtc tctctgaaag    27060
actgcttaag catctaactc cgtcatctgt ggtcttaact aacggtgtag cgaagtgtt    27120 tgcctatggt ggaaaccaag gagataacgt atggttcttg acttccggtc ttgtctacaa    27180
gctgagacct aaagagaagc tagagttcgt tcagcgaatc tctgagtaca gggacttaat    27240
```

```
gttagaccaa tacgggacca tctggaacta cgtgtggtca ggcaataagt ctcacattaa    27300
attcttgaag ttactaggcg ctaggtttca cgatgagtgg accacaagtc cggtaactgg    27360
tgagcgattt caattattca caatctctaa ggaggacgta tgtgcgagcc gactagcata    27420
ggcatgggta tcatggctgt agccggggct actatgtccg catctcaaca ggccaaggct    27480
gagggtgctg ctatcgacgc tcagaacaga caggctcagg aaatggttaa gcagatgaac    27540
tactctgacg ccaacctgag gatgcaggag cgagacctga aggaacagca gatgactgaa    27600
ctgacagaga ccactctcaa tggtatccgc aatcagggta tggtccgagc tgcggtagct    27660
gagtcaggtc tggaaggtaa ctctatggac aggattgaac gtcaggtcga gggagataca    27720
gtcaaggaga gagcagggat taccgaaagt tacaaccgcg actatgcggc tatcttcggg    27780
aaccgtatcg ccaacattga gaacaccaag tctgctatcc gcggtcaagg taaaatcatc    27840
aagaccagcc cactggctca tgcacttaat gttgctaacg ccgggatgca agggtacgct    27900
gctggtaagt caatctctgg ggcatcaagc tctggtggtg ctgcaccgat tagtgctgct    27960
aaaggcacac ctacaggtca tagctaagag gaggactaat ggctagtaat attgaatcag    28020
ctctggctaa tcggactatg ggtcgtggca gagcgcctgg taaaactatc gccgtcaact    28080
atcaagcagc caacgttcag gctccgactg gtgactctgg tctagctcgt gcgttaacca    28140
acttcgttga gtctgggact ggattataca agcagttcaa agacgaggag aagaccagag    28200
ctgatgagcg gtctaacgag attatccgta agttgacacc tcagcaaaga cgtgaggcta    28260
tccagaacgg gacactgcta tatcaggacg acccttacgc tatggaagca cttcgagtca    28320
agacgggccg taacgctgcc tttgcggtgg atgacgagat taacgttaag attcagaacg    28380
gtgagttccg tacacgtcag gacatggaag agtatcgcca ccagcgactt caggatgctg    28440
ctaagtccta tgctgaagag gcaggtatta accctaccga cgagttcttc cagcgtggat    28500
ttaacgataa catcactgac cgaaacatcg ctatctacgg gtcttttcaat aagtatttca    28560 gcaagcagtc tgaagagaca gcaatgttga acactcgtat tgagctgaac tcgttccttta    28620 acgatgggga cctgatgcgt tcgcctgagt ctggaaagac cttcatggcc taccttcggg    28680
atggactgac gactgctgct ataccttcgg accagagagc acgagaggtc atcacccaga    28740
cggtccgtga cgcaatccag aagtcaggag gctcaaactt cctacagcaa gtccgtggcg    28800
agcgtatcac ccttaatggt gttgacgcta ccatcgaaga ggttgtagga cctgacgtct    28860
tcaatgctgc tatggttgag gcccaaggta ctgagtataa actggtggct aagtatcagg    28920
aagacttggc gttaggagtt cagtctgcga ttcttcagga cgacccaacc atcggtcttg    28980
cccagattca gaaactcaag gagcagaaca accagcttca acccggcgaa gaactcactc    29040
ctcagcgtca gatgcttatt aatgccgaag ccagcttact tgaagcggta aaacgtaagt    29100
ctgctgaaca ggcgaaggag aacactaagt taatccagac tcagaacaag caactggtca    29160
ttgaccaagt gtatcagcga cgtctggctg gggacaacgt gtccaccaac tatgaggacc    29220
ttccggtatc tgaagctaca ggagagttca agcgttcaga catgaacaac tatgcgtctg    29280
ccaagctaca gcagattgac cagatggaca tccctgaggc tgctaaagat gctcagaagg    29340
tggcattgtt aagagctgac actaacaacg gtccttttccg taatgccttc cagacgctta    29400
ctcaggacgc tgctggtgag tggcaagctg cggtcatccg tggacagtac gacccagaca    29460
agatgaaacg cttcgagtct cttcgtcgtg cctacactca ggacccttca gtttcgctg    29520 ctctgtatcc tgaccaagct cagctgttct ctacgttcga ccagatggac aagatgggtc    29580
ttgaccctca gacgatgatt gaagctgata agcaagctgc aagtcaaagc cgtgagatgc    29640
```

```
gcatggaatc agacaaggcg tggcaggagt tgaagaacga ctccaagaac acccagttgt    29700
ctcgcctccc aacgtctctg gattcaagtg ctcgtaaggt ctgggactca tggtactatc    29760
gtacaggtaa cgctgatgct gcaactcagc agactcaacg ctggctgaac gagaacaccg    29820
taacgttcca gtctgaaggt tctgacggta agtcaatcgg catggtatcc aagcaccagc    29880
ttatggtcgg ggataaccct gagtcgtggc aggtaggtcg agacattatc gacaccgccc    29940
gtaagcagct cattaaggcc aacccttggg tagtgaactc tcagttgtcc gttgttgaac    30000
agaacggctc tatcttcctc caagacgcta caggtaccat tcgtattcgc tacgataagg    30060
aacttgtagg taaactctac cgcgaacaac agcagaaggc acaagatgcc gcatatgctc    30120
aggcagaacg tgacgctaac aagcgagcgc gtatcgtcgg gactaaagct gctggtgata    30180
aacgtcgagc tgaccgagag gccaacatcg agaagcgcgg tgggatgtac aatgacgtct    30240
cactggaggg tatcgcaaac gtattaattg gtaaggagta acataatggc gacacgtgga    30300
gtaaggaatt caaaccccgg gaacctccgt aagtccaaag accagtggga aggtgctata    30360
ggtgatgatg gtgaatttgt tatcttcgac agccctgaat ccggggtccg agccttagca    30420
aaaaaccttc aaagctacgg tcgccaaggc tacgactcaa tcgagaagat tatcagccgc    30480
tgggcaccac ctaatgagaa cgacactcag tcatacatca actctgttgt ggctgctact    30540
ggcattccag cgacccagag tctcgacctg acgaaccctg acgtcctcgc ctctctgtct    30600
gaggctatcg gctaccacga cacaggctcc cggtacgacc ctgaagtcta tcagaaggga    30660
gtcgcacggg cactcaacgg tatcaccca aagaccccac cagtaagcgc taacgtattt    30720
gacgctctca cggagggctt gaaggctaaa cctaaagtag ctctgggcga gaaccttccg    30780
accgctgctg gtctaaacat tgagggtcaa gcacctgaag ctcccaacga atcgttcggt    30840
gagatgttct ataaggctac tggagagacc atgcaggagc gagaggatcg ctctacgtgg    30900
ttcggtttcg gtgctgctgc agaagctgaa gtgaagaact ctatggtcgg cgtggctatc    30960
cgagctggtc agactgagga ttcactggat gtcattggtg atgtgttcaa cccgaccaga    31020
tggaacaacc ataagtggtc gcgtgaggag ctggaccaga ttcgtaacgc tggggttctg    31080
cctcagtatt acggagtcat tactggtggc tctcctcaga acctgaccga gcttattaac    31140
ttggcgcttg agaaccagaa gttggaccaa gagaaggcca aggctgggac tggcgctcag    31200
ttagctgctg gtgttattgg tgctggcgtg gaccctctga catacgttcc tattgctgga    31260
caggttggta aaggcgctaa gctggtcaat aagatgttca ccgtggctgc tcaatctgga    31320
gcactggctg gtgtgtctga gatggcccgt acctcagtgg ctggtggtga tgctcatgtg    31380
gcggaagcta tccttggtgg tgctctcttc ggtggtggta tgactgctat cgctgatgga    31440
ctaggcagag ccttaggtcg caacactaat gagttcgctg cccagctac acgtctggaa    31500 gctcgtgaga ccgctcgtaa cgttgatggt caggacctgt ctcgtctccc tattcaggaa    31560
ggtgagcaga cctttagtca tcaaggcgtt aagttcgctg acgttccgaa cgagtcgggt    31620
agtgtacgac ttgaagatgg ttcaatcctg attggtgaga accctctgaa ccctaagaca    31680
cgtcaggtct ttgatgaagt gattgagcct gaacgtgctg ctgctggtgt gaaccttggt    31740
gggctgactg agattggcct gaagcttctt cggtccgaga accctgagat tcgtggagtc    31800
gctgctgact tagtgcgttc accgactggt atgcagtcag gggcctcagg taaaatcggg    31860
accactgcgt cagacgtatt cgagagactt cgtgctgtgg accatcggtt ctacaacgac    31920
atcgacgatg cggttactga ggcgctcaag gacccatact tccagacagc attctggcga    31980
```

```
gactctggcg cattccgtca ggacatctac caacgtgtgt ctatggctat agaagatggt   32040
agcgggaacc tgaagtctga actgactccg ggagaactga aagtctacga cctgctgaag   32100
aaccagtttg acgccaagcg tgagatgatg gagaacccag cgatgtttgg tcgtccagac   32160
gctaagtcta tctttccggg tagtcgcttc aagggaacct acgtcccgca tgtgtatagc   32220
aaccagatga aggagctgta catcaaggag cttggaagtc agaggcact acaggaggcc   32280 atcaagaagt catggttgac cagctatgcg tctcggcctg aagtcaagaa acgtgtggac   32340
gaggcactct tagaggctga ccctactctg actccagagg gacttgctgc tgcggtcgat   32400
aagtacgcca acgataaggc ttacggtatc tctcacaccg agcagttcga acgttcatcc   32460
gtaatggaag agaacatcaa cggtctggtg ggtcttgaga acaacagctt ccttgaggct   32520
cgtaacctgt tcgatagcga tatgtcaatc gttctgccta acggtcagac cttcagtgtc   32580
aacaacctgc gtgagtggga catggacaag attgtcccgg cctacaaccg tcgagttaat   32640
ggtgacattg ctatcatggc tggtacaggc aagaccacga aggacatgaa ggacttagtt   32700
gagaccatga tgaacaaggc tggtgatgat ggcaagttga aggtgaggt ctcgaccta   32760 cgagacacct tgaagattct cactggtcgt gctagacgtg atggtgctga cgatgctgcc   32820
ttcgctacag tgatgcgcac aatgacagac ctatcgttct tcgctaagaa tgcctacatg   32880
ggtgttcaga acttaacgga gattggcggt atgctggctc gtggcaacgt tcgtgcaatg   32940
ctgcatggag tcccgatgtt ccgtgaccta gccttccgta caagaaggt cggggcctca   33000 gagattaagg acctgcacaa tgttatcttc ggtaaagaac tggatgactc aatccgtccg   33060
tctaaacagg acgtcattga ccgtctgcga gcttacagtg acctcggtcg tggtacagct   33120
acagctcttg ggactgccaa gtattacact ggtgaacttg cagtacgctc tccgttcact   33180
aaagtcctga acgtacgac taactacctg cttgatgctg gacgtcaggg cttcttgtct   33240
gacatagtgg agcacagcct gaccggaagt aagcgtaagt ttgatgaccg ctggttgaag   33300
accgctggta tctccgctga ccagtggaag ggcattaagt ccctcatccg tgagtcagtg   33360
actcgtggtc cagacgggaa gtacaccatc aaggataaga aggcgttcag tcaggaccca   33420
agggctatgg acctctggcg catgggtgac accatcgctg atgagaccct cctccgtcct   33480
cacaagctga gcaacatgga tgcaaaggct tatggaccgc tggctaagac tgtcttgcag   33540
tttaagaact tcgtcatcaa gtctatcaac ggtcgtacaa tgcggaccta ctacaacgcc   33600
accaagaaca accgagctat tgacgctgcg ctgtccacgg tgatgtctat gggtctggct   33660
ggtatgtact acatggctca ggcgcacatc aaggcctacg ctatgcagga tggccgcgac   33720
cgtgagtacc tgaagcaggc gcttaaccct acgatgattg gctatgcggc tctgtcccgt   33780
agctcacact gggtggccc actcggggtc gctaacattc taggtggcat cgctgggtat   33840
gaggacacta agcttctccg ttcgtctatc ctccctcgtt cacctacaga gaagcctgaa   33900
cgtgccatcc cgtatggtgc ggctacaagt gaccctgtga tgaatgtcgt cggtaacttc   33960
ttggagcagg ttccagcttt cggctatgct gctaacgttg gtgcttcggc ttacaacttg   34020
gctggctacc taaaggccga tactcgtgtc aacgagcgag actatatgac aggtatgtat   34080
aataccttcc gagaactagt cccgaacgac ccaattactc agaagctact gcttgggacc   34140
ttcgaggagc aaggcatcca catcaaagac taaactatca ctataggaaa cgggacacta   34200
acataggtcc ctcttatgtc aaactaaagg aggccaaatg tcaggcactt taactcagtt   34260
ccctacaggg agcactcagt ataaaattaa cttcgagtac ctagctcgtg cattcgtggt   34320
cgtgactttg gtcaactctt ctgataactc tcagaaccgt gtactgactg tgggcaatga   34380
```

```
ctacacgttc cttaaccta cgacaatcta tgtaactgct aaccaagccg gttatgacat    34440
tatacagatt caccgtgaga ctactacaga acttatcgtt gacttccgtg atggctcagt    34500
cctgactgct agtgatttaa ctaacgctga gcttcaggct gtccatatcg cagaagaggg    34560
taaggaccag actattgaac ggggtcgaca gtatgctgaa gctgctggaa agaatatga    34620 gaacgctaag tctgagcgcg aagctattga ggacattgtt tcaacttctg gctgggactc    34680
taagttgcgt tctgatttag caggggctga tggatacaca ttagtgccta ctgttgcgcc    34740
taagaactca gtaacaagag tgcccattac gacgttccct tcgtataata attcagctat    34800
tgagcaagca atgtatgact cggtgcagac tctgggatat gcatacatcc ccggcctagg    34860
cgcggaatac actaagtata caatctcaaa cactatatca ccctcagtag atttaacagg    34920
tgcgcgcgtg attgtagacg atatggtttg gatagattca aactatgaca actactcatt    34980
ctttaaatcg ttaaactttg agggcaagtg taagtttact ttcagaaacg gattgtttgg    35040
gatgactggt ggtgaggttg aagccttacc taacgtcgga cgactaaatg aatctccagt    35100
atccatctcc cctatatcgt tcgatgatac gtatgtacgt attctacaga gtgacctaga    35160
tactttctcc accggggtta aaggagcttc taatgattac tcctgtgagt ttgcagttga    35220
agctggtaag tatgctggat tgtttaccgg aataaatatt ggtgagacga taacagggca    35280
tataggagca gcgcacggac aggaaaaagc tgaatcgaca ggtgtcttac tccgtggaga    35340
actaggatgg attctattcg acggatttag taatgggagt gagtggcgtt acagggttaa    35400
gaagaaaggc gaatcaatgg taaatggtgc gtcaatttcc gtacctgagt ctggaatgct    35460
taaatcgtac tctccgtcca atgctacagt tggtattagc cttacagcag cggacagatt    35520
caactttatt gtcaatgggg taagtttgac cccaacattc acatcactag taggatccat    35580
ttatgagata ggattcgtta gttcgaacca aactactatg atgcagagag taacaggcct    35640
gaatctctac acatcaaagc gaggagtctt tgggcatgct cctcttcaca tcttgatacg    35700
tggagattct accgcagaag gattcatctc tacttttgac aagtatctac cgggtcttct    35760
cgacggctcc atgggtacac gcagtttatc aattactaac aaggctattg ctggtgcgtt    35820
catgcgtcag cagcttgacg accttaaggc tgaaggcgct ggacaggcat atatggtaat    35880
catggttggt ggaactaatg aagggcaagc taactacagt cctgacgcgt tcggcgcaat    35940
ggttaaggag tttgctgatt ggtgcattc taatggtaga gttcctgtct gggttgagcc    36000
gtggatgtgg tattcgaaga cattcgtagg aggtgcagga caagactcta gtaactacga    36060
gaatgctgca caattgcgag agtcaggtaa aagggctatg gcttcttatg agacctcgg    36120 tatatgcgtt ccgacgacac acatactgcc agcacctatg cctgagtatg taacatctgg    36180
tgttgctcca ctattacgtg atgatattca ccaagatgag ttagggtata aactctatgc    36240
cgaagccatt gcgtccgcga tagtaggctg gtcgtccaag gtatcatcta ggccacgtcc    36300
agcatggagc gaatggtctc gcaatacagc ttcaataacg tacccatcca tagtaaccac    36360
taatagtatt aacgtatcta tggacatcac tggcttctca aatggacagg ttgtacttaa    36420
cctaccacga gggtgccgtc cagtggttac tacggtagcg actgttacac acactactga    36480
taacatcaac tatgctgctg gtttcgctct aatagctcct aatggcgacg tgactgtgca    36540
ggggcttaag tcgacagaag gtcgcataac tattgtagca aattggtaaa taactggagg    36600
ccttatgatt gagttagact tcaagaatga agttcttaag gcctcccta tcgttgggac    36660 cgctgcggct gatggtgcca gtcggttctt ctttggactc acactgaacg aatggttcta    36720
```

```
cgttgcagct attgcgtaca ccgttgtcca gattggtgtg ctggtctaca aaacgattaa   36780
aggggaggga aagtcatgac acaaatggac ttagagaagt tcctgttaat gctagataca   36840
gagcgtgccc gtctcatgct gcaagacctg cgggatgaca ctaagcgttc acctcagctc   36900
tacaacgcca ttgagaagct actagctcgt cacaactttg tgttaagcaa ggtgtctgtg   36960
gacgagaaga cgctggctga tatggaggcc ctgaacgcag agtacgataa ggtgctttca   37020
gctactgagg ataatgacac cgggtatggt gttcaataag tgttagactc aaggtcatcg   37080
tcaggtggcc tttatgatta acactaagga ggttacatga aagattcata cataagtggc   37140
ggttactgga aggttactcg taacggtaag gttcatggag ttcatagatt actatgggag   37200
gaagcctacg gtactatccc agatggttac gtcatagacc acattgatag gaatcctatg   37260
aataacgaac tgtcaaacct taggtgcata cctaaaggcg caaacaaggc taacacggta   37320
tcctctaggg aactacctaa aggcgtatac tctaggtttg ctaaacgtca aggtgtaact   37380
gtgtactatg gtgacattag gatgggaggt aagaaagaaa ctcatgcgcc tactaagaat   37440
ctgaaggaag tcgtggaatg ggctaagtca actcatagca gaatgctaaa ggagacatat   37500
ggtatttcaa atgtttaaga gagtggctcc gtggttactt gcagcagtga tgtttgctgg   37560
tggctaccac accgctaaca ataagtggga ggctaaggtc aatgcagaat acacctcgaa   37620
tcttaaggca tcggaggata caaggcttgc tgtccaagct gaagtcaaca aagtgtcaaa   37680
gcggtttcag gacgaaatgt cctcgctgga aggcagcact gataggatta ttgctgacct   37740
tcagtctgac aataagcggc tgcgcatccg agtcaaacct acgagtggag ccacgcaaag   37800
tgacggtcga tgcgtcattg atggttacgc cgaacttgac gaacgagatg ctaaacgtct   37860
tatcgccatc ggagtgaaag gagacaaatg gattaaggca cttcaggaca ctgtgagagc   37920
cttacagcaa gataaggagg ggacgcattg agtaaagact tagtggcgcg tcaggcgcta   37980
atgactgccc gtatgaaggc agacttcgtg ttcttcctgt tcgtcctgtg gaaagctctg   38040
tcactaccag tcccgactcg ctgtcagatt gacatggcga agaaactatc ggctggggac   38100
aacaggcgtt tcatcctaca ggcgttccgt ggtatcggga agtccttcat acgtgtgcc    38160 ttcgtggtct ggaagctatg gaacaaccca gacttgaagt tcatgattgt gtcggcctca   38220
aaggaacgag ccgatgcgaa ctccatattc atcaagcgaa tcatcgacct catgcctcag   38280
cttcaggaac tcaaacctaa gcagggacag agggacgcgg ttatcagctt cgacgttggg   38340
ccagccaagc cggaccactc accttcggtt aagtccgttg gtatcactgg tcagctgact   38400
ggtagtcgtg ctgacatcct gattgccgat gacgtggagg ttccaaacaa ctctgcgact   38460
caggctgcac gagaccgtct gtcagagctt gtgaaagagt tcgacgctat cctgaagccg   38520
ggaggtacaa tcatctatct gggtactcct cagaacgaga tgaccctgta tcgtgagctt   38580
gaaggccgtg gtataccac tactatctgg cctgctcgtt atcctcgtga taagaaggac    38640
tggcagtctt acggcgaccg tctggctcct atgcttcagg cagaactgga agaggaccct   38700
gagtccttct actggcgtcc gaccgatgaa gtacgattcg atgatacgga cctgaaggaa   38760
cgtgagctgt cctatggtaa agctggcttc gctctacagt tcatgcttaa cccgaacctg   38820
agtgatgctg agaagtaccc tctgaagctc cgtgacctta tcgtagccga cttgacccca   38880
gcgtccagcc caatggtcta ccaatggctg ccaaaccctc agaacaagcg tgaggacgtt   38940
cctaacgttg gactcatggg tgactcatac cacacgtatc agactgtagg ttctgccttc   39000
agttcgtaca cccagaagat tctggtcatt gaccctagtg gtcgtggtaa ggatgaaact   39060
ggttatgcgg tactgtacca gctcaacgga tacatcttcg ctatggaagt tggtggtatg   39120
```

```
cgaggtggct atgaagactc tacgctggaa gccttggcta agattggtcg taagtggaag    39180
gtcaacgaat acgtcattga gggtaacttc ggtgatggta tgtaccttga gctattcaag    39240
cctgtagcgg cacgtatcca ccctgcggct gtaactgaag tgaagagtaa gggtcagaaa    39300
gaactacgca tctgtgacgt tctggagcct atcatgdgdt ctcacaggct tatcgttaac    39360
gctgctgcta tcgtccaaga ctaccagtca gcctctgata aggatggtgt gcgtaaccct    39420
atctactctc tcttctacca gatgacccgt atatctcgtg aacgtggagc cttggcacac    39480
gatgaccgac ttgatgcgct ggctatcggt gtacagttct tcgttgagtc tatggctaag    39540
gatgccaaca aaggcgaacg tgaagtcact gaggagtggc tggaggaaca gatggaggac    39600
ccacggaaag gcttcgagtc catccacact gagttctggg acaatggggt ccgggtaact    39660
catgatacgg acgacgagct gggactaggg tcatacgtta cgttccacta gctgaatgaa    39720
taactatggg tgaaagctgc atgaatacgc ggttagtaac ctatagttac taccagtcta    39780
acctactgtt ttataagaag tttggactta actatcacta taggaaagac caatggttac    39840
ttatagtatt actgtagtga atatacatat gcagacttta tgcaagacct taggaggcag    39900
actccgagtt cttacctaag gcttgcaccg atggaaggag gtgatattaa tcataatccc    39960
tccaatacag atagtcaccg accatagata caggaggtat gtagcatatg gcaaagacca    40020
aagctgtact taaagctctg gcgaccaatc gagctacata caggtttctt gctgctgttc    40080
tacttgctgc tggcgttact gctggaagta agtgggtcgg gtgggtcgag actctcgtat    40140
gttctctggt ctctcagtgt aattaacgca atcatggtaa cgattcatga gtggaagacc    40200
taaggtcagt tcatagctga cgctactcta ctgaccttag ctactgtagt caaggacttt    40260
aggtaacacc ttaagagaag ctcacttagg gtcatcctac ttactggtct accctagtgt    40320
cgcctgacct acggtccttg acctacagtg gctgtggcct acagtaggga cgatgagttt    40380
tggaccaaaa gtttgagacc aca                                            40403
```